(12) United States Patent
Anderson

(10) Patent No.: US 9,149,244 B2
(45) Date of Patent: Oct. 6, 2015

(54) VOXEL-RESOLUTION MYOCARDIAL BLOOD FLOW ANALYSIS

(75) Inventor: John M. M. Anderson, Washington, DC (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 14/008,021

(22) PCT Filed: Mar. 29, 2012

(86) PCT No.: PCT/US2012/031263
§ 371 (c)(1),
(2), (4) Date: Sep. 27, 2013

(87) PCT Pub. No.: WO2012/135526
PCT Pub. Date: Oct. 4, 2012

(65) Prior Publication Data
US 2014/0016850 A1   Jan. 16, 2014

Related U.S. Application Data

(60) Provisional application No. 61/468,765, filed on Mar. 29, 2011.

(51) Int. Cl.
*A61B 6/00* (2006.01)
*A61B 5/0275* (2006.01)
(Continued)

(52) U.S. Cl.
CPC ........... *A61B 6/5217* (2013.01); *A61B 5/02755* (2013.01); *A61B 6/037* (2013.01);
(Continued)

(58) Field of Classification Search
CPC ........ A61B 6/481; A61B 6/504; A61B 8/065; G06T 7/0012; G06T 2207/30101; G06F 19/3437
See application file for complete search history.

(56) References Cited

U.S. PATENT DOCUMENTS 5,070,877 A   12/1991   Mohiuddin et al.
5,135,000 A   8/1992   Akselrod et al.
(Continued)

FOREIGN PATENT DOCUMENTS

WO   2012135526   10/2012
WO   2014130566   8/2014

OTHER PUBLICATIONS

Candes, E., et al.; "Enhancing Sparsity by Reweighted l1 Minimization"; Research paper; Oct. 2007; 28 pages.
(Continued)

*Primary Examiner* — Amir Alavi
*Assistant Examiner* — Kenny Cese
(74) *Attorney, Agent, or Firm* — Fitch, Even, Tabin & Flannery LLP

(57) ABSTRACT

A myocardial blood flow analysis scan includes incorporating a pharmacological kinetic model with the standard factor analysis model where each time activity curve is assumed to be a linear combination of factor curves. Pharmacological kinetics based factor analysis of dynamic structures (K-FADS) model can be applied, whereby a means for estimating factor curves in the myocardium that are physiologically meaningful is provided. Additional optional aspects include performing a discretization to transform continuous-time K-FADS model into a discretetime K-FADS model and application of an iterative Voxel-Resolution myocardial blood flow (V-MBF) algorithm. A V-MBF algorithm based on a model that accounts for the fact that the shape of TACs due to ischemic and normal tissue are different can be included.

27 Claims, 2 Drawing Sheets

(51) Int. Cl.
 A61B 6/03 (2006.01)
 G06T 7/00 (2006.01)
(52) U.S. Cl.
 CPC ............... *A61B 6/481* (2013.01); *A61B 6/503* (2013.01); *A61B 6/507* (2013.01); *G06T 7/0016* (2013.01); *G06T 2207/10104* (2013.01); *G06T 2207/30104* (2013.01)

(56) References Cited

U.S. PATENT DOCUMENTS

| | | | |
|---|---|---|---|
| 5,732,707 | A | 3/1998 | Widder et al. |
| 7,127,095 | B2 | 10/2006 | El Fakhri et al. |
| 7,519,211 | B2 | 4/2009 | El Fakhri et al. |
| 7,804,440 | B1 | 9/2010 | Orr |
| 8,207,886 | B2 | 6/2012 | Chambers |
| 2003/0048937 | A1* | 3/2003 | Gullberg et al. ............. 382/131 |
| 2006/0022866 | A1 | 2/2006 | Walton et al. |
| 2006/0104410 | A1 | 5/2006 | Sauer et al. |
| 2006/0187305 | A1 | 8/2006 | Trivedi |
| 2008/0230703 | A1 | 9/2008 | Kadrmas et al. |
| 2009/0226064 | A1 | 9/2009 | El Fakhri et al. |
| 2010/0060509 | A1 | 3/2010 | Chambers et al. |
| 2010/0140483 | A1* | 6/2010 | Rousso et al. ............... 250/362 |
| 2010/0312118 | A1 | 12/2010 | Horzewski |
| 2011/0128816 | A1 | 6/2011 | Baba et al. |
| 2011/0150309 | A1 | 6/2011 | Barfett |
| 2012/0019406 | A1 | 1/2012 | Sarkis |
| 2013/0004044 | A1 | 1/2013 | Ross |
| 2014/0016850 | A1 | 1/2014 | Anderson |
| 2014/0236004 | A1 | 8/2014 | Rognin |

OTHER PUBLICATIONS

Chen, S., et al.; "Atomic Decomposition by Basis Pursuit"; SIAM Journal on Scientific Computing; vol. 43, No. 1, pp. 129-159; 2001.
Davis, G., et al.; "Adaptive Greedy Approximations"; Constructive Approximation; vol. 13, No. 1; 1997; 47 pages.
De Leeuw, J., et al.; "Sharp Quadratic Majorization in One Dimension"; Computational Statistics and Data Analysis; vol. 53, No. 1; 2009; 14 pages.
De Pierro, A.; "A Modified Expectation Maximization Algorithm for Penalized Likelihood Estimation in Emission Tomography"; IEEE Transactions on Medical Imaging; vol. 14, No. 1, pp. 132-137; Mar. 1995.
European Patent Office Extended European Search Report dated Jul. 17, 2014 for European Application No. 12764542.2; 7 pages.
Figueiredo, M., et al.; "Wavelet-Based Image Estimation: An Empirical Bayes Approach Using Jeffrey's Noninformative Prior"; IEEE Transactions on Image Processing; vol. 10, No. 9, pp. 1322-1331; Sep. 2001.
Hove, J., et al.; "Dual Spillover Problem in the Myocardial Septum with Nitrogen-13-Ammonia Flow Quantitation"; The Journal of Nuclear Medicine; vol. 39, pp. 591-598; Apr. 1998.
Hunter, D., et al.; "A Tutorial on MM Algorithms"; The American Statistician; vol. 58, pp. 30-37; Feb. 2004.
Hutchins, G., et al.; "Noninvasive Quantification of Regional Blood Flow in the Human Heart Using N-13 Ammonia and Dynamic Positron Emission Tomographic imaging"; JACC; vol. 15, No. 5, pp. 1032-1042; Apr. 1990.
Klein, R., et al.; "Kinetic model-based factor analysis of dynamic sequences for 82-rubidium cardiac positron emission tomograph"; Medical Physics; vol. 37, No. 8, pp. 3995-4010; Aug. 2010.
Metje, N., et al.; "Mapping the Underworld—State-of-the-art review"; Tunnelling and Underground Space Technology; vol. 22, pp. 568-586; 2007.
Nguyen, L. et al., "Mine Field Detection Algorithm Utilizing Data From an Ultrawideband Wide-Area Surveillance Radar"; Proc. SPIE 3392, Detection and Remediation Technologies for Mines and Minelike Targets III; vol. 3392, pp. 627-643; Apr. 1998.

Nguyen, L., et al.; "Supperssion of Sidelobes and Noise in Airborner SAR Imagery Using the Recursive Sidelobe Minimization Technique"; U.S. Army Research Laboratory; IEEE Radar Conference; pp. 522-525; May 2010.
Nguyen, L., et al.; "Obstacle Avoidance and Concealed Target Detection Using the Army Research Lab Ultra-Wideband Synchronous Impulse Reconstruction (UWB SIRE) Forward Imaging Radar"; U.S Army Research Laboratory; Proc of SPIE vol. 6553; 2007; 8 pages.
Nguyen. L., et al.; "Signal Processing Techniques for Forward Imaging Using Ultra-Wideband Synthetic Aperture Radar"; U.S. Army Research Laboratory; Proc of SPIE vol. 5083, pp. 505-518; 2003.
Nguyen, L.; "Image Resolution Computation for Ultra-Wideband (UWB) Synchronous Impulse Reconstruction (SIRE) Radar"; Army Research Laboratory; Sep. 2007; 26 pages.
Nguyen, L.; "Signal and Image Processing Algorithms for U.S. Army Research Laboratory Ultra-wideband (UWB) Synchronous Impulse Re-construction (SIRE) Radar"; Army Research Lab; pp. 35-38; Apr. 2009.
Nguyen, L.; "SAR Imaging Techniques for Reduction of Sidelobes and Noise"; Army Research Laboratory; Proc of SPIE vol. 7308; 2009; 12 pages.
Notification Concerning Transmittal of International Preliminary Report on Patentability from the International Bureau of WIPO for International Application No. PCT/US2012/031263 dated Oct. 10, 2013, 5 pages.
Notification of Transmittal of the International Search Report and the Written Opinion of the International Searching Authority, or the Declaration from the International Bureau of WIPO for International Application No. PCT/US2012/031263 dated Oct. 30, 2012; 8 pages.
Notification of Transmittal of the International Search Report and the Written Opinion of the International Searching Authority, or the Declaration from the International Bureau of WIPO for International Application No. PCT/US2014/017185 dated Jun. 10, 2014; 17 pages.
Potter, L., et al.; "Sparsity and Compressed Sensing in Radar Imaging"; Proceedings of the IEEE, vol. 98, No. 6, pp. 1006-1020; Jun. 2010.
Ressler, M., et al.; "The Army Research Laboratory (ARL) Synchronous Impulse Reconstruction (SIRE) Forward-Looking Radar"; Proc. of SPIE vol. 6561; 2007; 12 pages.
Schmidt, M.; "Least Squares Optimization with L1-Norm Regularization"; Project Report; Dec. 2005; 12 pages.
Tan, X., et al.; "Sparse Learning via Iterative Minimization With Application to MIMO Radar Imaging"; IEEE Transactions on Siginal Processing; vol. 59, No. 3, pp. 1088-1101; Feb. 2011.
Tibshirani, R.; "Regression Shrinkage and Selection via the Lasso"; Journal of Royal Statistical Society; Series B, vol. 58, No. 1, pp. 267-288; 1996.
Vaida, F.; "Parameter Convergence for EM and MM Algorithms"; Statistica Sinica; vol. 15, No. 3, pp. 831-840; 2005.
Van Der Merwe, A., et al.; "A Clutter Reduction Technique for GPR Data from Mine Like Targets"; Proc. SPIE vol. 3719; Aug. 1999; 12 pages.
Wu, C.; "On the Convergence Properties of the EM Algorithm"; The Annals of Statistics; vol. 11, No. 1, pp. 95-103; Mar. 1983.
Wu, T.T., et al.; "The MM Alternative to EM"; Statistical Science; vol. 25, No. 4, pp. 492-505; Apr. 2011.
Wu, Z., et al.; "An Image Reconstruction Method Using GPR Data"; IEEE Transactions on Geoscience and Remote Sensing; vol. 37, No. 1; Jan. 1999; 8 pages.
Yang, A., et al.; "Fast L1-Minimization Algorithms and an Application in Robust Face Recognition: A Review"; Technical Report No. UCB/EECS-2010-13; Feb. 2010; 14 pages.
Yang, A., et al.; "Fast I1-Minimization Algorithms for Robust Face Recognition"; IEEE Transactions on Image Processing; vol. 22, No. 8, pp. 3234-3246; Jun. 2013.
Notification of Transmittal of the International Search Report and the Written Opinion of the International Searching Authority, or the Declaration from the International Bureau of WIPO for International Application No. PCT/US2014/059062 dated Jan. 14, 2015; 11 pages.
Notification of Transmittal of the International Search Report and the Written Opinion of the International Searching Authority, or the Declaration from the International Bureau of WIPO for International Application No. PCT/US14/42562 dated Mar. 18, 2015; 10 pages.

* cited by examiner

VOXEL-RESOLUTION MYOCARDIAL BLOOD FLOW ANALYSIS

RELATED APPLICATION

This application is the National Stage of International Application No. PCT/US2012/031263, filed Mar. 29, 2012, which claims the benefit of U.S. Provisional application No. 61/468,765, filed Mar. 29, 2011, each of which is incorporated by reference in their entireties.

TECHNICAL FIELD

This invention relates generally to estimating myocardial blood flow (MBF) and more specifically to a positron emission tomography (PET) based method for estimating myocardial blood flow (MBF) using a ventricle curve starting assumption.

BACKGROUND

Imaging of blood flow through the heart and associated veins can improve diagnosis and treatment of cardiac diseases. In particular, estimation of myocardial blood flow or blood flow through heart muscular tissue can be useful as described below.

By one approach, nuclear based medicine can be used to produce useful medical images. In such an approach, radioactive elements are introduced into the bloodstream such that when the radioactive elements experience a radioactive decay, the byproducts of that decay (often the reaction with particles called positrons) can be sensed to produce an image of the area where the radioactive elements are placed. An example approach to this kind of imaging is called positron emission tomography (PET). Several radioactive elements, called positron emitting tracers, are available for these studies with the most common being $^{82}$Rb and $^{13}$N-Ammonia.

Currently, PET is a primary method for determining non invasive coronary flow reserve. Coronary flow reserve can be defined as a ratio of a maximum hyperemic flow to baseline flow. In normal patients this ratio can typically range between 3-5, which is a essentially a measure of the function of coronary circulation and is particularly useful in the detection of early abnormalities due to coronary artery disease. Because the coronary flow reserve determination is a ratio, it is unaffected by a uniform reduction in both baseline and maximal flow.

Unfortunately, coronary flow reserve does not reflect true vasodilation capacity. A reduction in coronary flow reserve could be caused either by increased flow in the baseline state or by reduced maximum hyperemic flow. Factors that increase myocardial oxygen demand, for example hypertension, increased left ventricular wall stress, increases in inotropic state, and tachycardia, can lead to an increased basal flow. Differentiating between this case and the reduced maximal hyperemic flow due to significant coronary stenosis is difficult without absolute myocardial blood flow measurements. Measurements of hyperemic blood flow in absolute units provide a more direct estimate of vasodilation capacity. Accordingly, only by accurate determination of absolute myocardial blood flow can the existence of uniform diffuse disease be determined.

Since the early 1990's there have been validated techniques for estimating absolute myocardial blood flow. Nevertheless, absolute myocardail flow estimation has not been adopted for routine use in a clinic setting because of technical limitations. These limitations can include lack of technical expertise in a clinical setting, time taken to perform the calculations, and the lack of widely available commercial products to perform the calculations and display the results. On the other hand, numerous reports indicate the effect on absolute myocardial blood flow of various interventions or conditions. Yet, calculating absolute blood flow for clinical studies remains rare. The result is that diagnostic decisions are usually based on relative myocardial blood flow or relative changes in myocardial blood flow between rest and stress, often aided by a software tool that compares images to a normal database.

There are at least three different kinetic models that have been used to understand the distribution over time of flow tracers in myocardial tissue. These works include spillover correction because of a finite resolution of the scanner and because the myocardium is moving during the scan. In one known approach, factor analysis was used to obtain spillover independent time activity curves of the right ventricle (RV) and left ventricle (LV) and myocardial blood tissue. By using curves generated from factor analysis, the spillover component in the model can be eliminated in theory; however, factor analysis does not correct for the under measurement due to the partial volume effect. Correction for this would require the use of a contrast recovery coefficient. Methods for addressing the non-uniqueness problem of kinetic modeling have been proposed. Also, kinetic modeling directly from sinograms from a dynamic sequence has been suggested.

In the following, let $a_{ij}$ denote the activity in voxel i of frame j. In factor analysis, it is assumed that the activity is a linear combination of K primary factor curves, where the summation coefficients are $$a_{ij} = \sum_{k=1}^{K} c_{ik} f_{kj}. \qquad (1)$$

The primary factor curves for this application are the right ventricular blood pool, the left ventricular blood pool, and the myocardial tissue curve. The mathematical task is to find both the factors and coefficients so that the linear combination of factor curves for every pixel in the image matches the measured curve as close as possible. This problem is constrained by requiring that the tissue curves and the linear coefficients are all positive.

Ammonia or Rubidium uptake is generally analyzed with a two or three compartment model. The models all have a blood compartment in contact with an extracellular free distribution compartment, which is in turn in contact with a metabolically trapped compartment. These models are much easier to calculate if it is assumed that the clearance from the metabolically trapped compartment is zero (or near zero) over the duration of the experiment. As a result, for accurate myocardial blood flow modeling, several authors recommend collecting and analyzing only two minutes of data. When using smooth data generated by averaging all pixels within a large range of interest, this is a reasonable approach.

While there have been significant advances in the art, further advances are possible. For example, it is desirable to have a myocardial blood flow analysis with greater acuracy than is presently known in the art.

SUMMARY

Generally speaking, pursuant to these various embodiments, techniques for estimating myocardial blood flow (MBF) in each voxel in the myocardium, and specifically to a method for estimating myocardial blood flow in each voxel in the myocardium using a model using pharmacological kinetics based factor analysis of dynamic structures (K-FADS) and using a discretization that transforms the continuous-time K-FADS model into a discrete-time K-FADS model, then applying an iterative algorithm, such as a Voxel-Resolution myocardial blood flow (V-MBF) algorithm.

In one approach, a myocardial blood flow analysis includes a processing device applying a pharmacological kinetic model to a data set stored in a storage device. The data set may be compiled from a PET scan or other imaging approach that can monitor fluid flow in a voxel set. For example, the data set may be derived from an imaging technique based on monitoring fluid based tracers in a left ventricle, a right ventricle, and myocardium of a patient or animal subject. By one aspect, the pharmacological kinetic model includes incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle. The processing device is configured to output a processed data set based on the application of the pharmacological kinetic model to the data set for providing a representation of blood flow in the myocardium. The processed data set may be usable to create a visual representation, an audio representation, a textural description of the myocardial blood flow using known methods for conveying such information.

In other aspects, the processing device optionally estimates parameters of the standard factor analysis of dynamic structures model by applying a penalty term to account for time activity curves for the right ventricle imaging activity from the fluid based tracers and the left ventricle imaging activity from the fluid based tracers decaying to zero over time. The estimating may also be done by estimating maximum values of fluid based tracer activity in one or both of the right ventricle or the left ventricle and modifying a corresponding signal vector value for the one of the right ventricle or the left ventricle using the estimated maximum values of fluid based tracer activity. In still another approach, the estimating may be done by estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve and determining a set of parameters that produce a smallest least-squares error for the pharmacological kinetic model. This estimation may include for a given initial estimate right ventricle tissue activity curve and a given initial estimated left ventricle tissue activity curve, determining initial estimates for parameters of the pharmacological kinetic model.

So configured, a more accurate derivation of myocardial blood flow is possible through the application of these modeling techniques. The advantages include increased resolutions and incorporation of kinetics. Further, unlike most known iterative algorithms for MBF estimation, such approaches explicitly describe a general procedure for initializing such algorithms. Other features will become more apparent to persons having ordinary skill in the art from the following description and claims.

BRIEF DESCRIPTION OF THE DRAWINGS

The foregoing features, as well as other features, will become apparent with reference to the description and figures below, in which like numerals represent elements, and in which.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A method and apparatus for estimating myocardial blood flow (MBF) in each voxel in the myocardium is described. The algorithm is based on a factor analysis of dynamic structures (FADS) model that has been enhanced to constrain the factor analysis curves to be physiologically appropriate.

Figure 1:
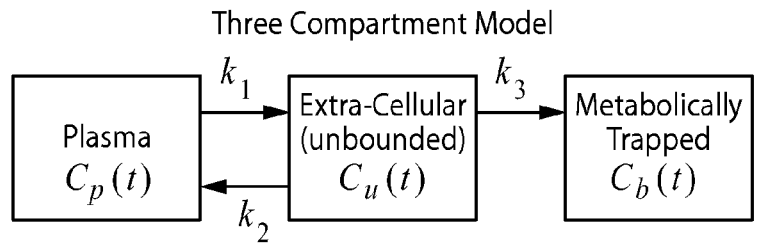
FIG. 1 illustrates a generalization of a 3-compartment model used to model Rubidium or Ammonia kinetics in the heart.

Turning now the figures, FIG. 1 illustrates a generalization of a 3-compartment model used to model Rubidium or Ammonia kinetics in the heart. Tracer in the second compartment is freely diffusible, while the tracer in the third compartment is trapped. The unknown parameters $k_1$, $k_2$, and $k_3$ are first order rate constants that describe the tracer movement between the compartments. The parameter $k_1$ (ml/min/g) is identified as myocardial blood flow. A first approach to analyzing MBF will now be described.

I. A First Approach

The kinetic behavior of ammonia in the myocardium is modeled with the compartment model shown in FIG. 1 and the following differential equations (note: assume $k_4=0$):

$$\frac{dC_u(t)}{dt} = k_1 C_p(t) - (k_2 + k_3) C_u(t) \quad (2)$$

$$\frac{dC_b}{dt} = k_3 C_u(t), \quad (3)$$

where $C_p$ is the ammonia concentration in blood plasma, $C_u$ is the concentration of the free (i.e., unbound) ammonia, and $C_b$ is the concentration of the trapped (i.e., bound) ammonia.

In one approach, a model is applied that incorporates a pharmacological kinetic model with the standard FADS model, which is a model where each time activity curve is assumed to be a linear combination of factor curves. The resulting model, which can be called the pharmacological kinetics based factor analysis of dynamic structures (K-FADS) model, provides a means for estimating factor curves in the myocardium that are physiologically meaningful. Further, a discretization is performed to transform continuous-time K-FADS model into a discrete-time K-FADS model. It should be noted that there is a simple relationship between the discrete-time and continuous-time K-FADS parameters.

Next, an iterative algorithm can be applied, such as the Voxel-Resolution myocardial blood flow (V-MBF) algorithm. This algorithm can iteratively estimate the MBF for each voxel in the myocardium. The V-MBF algorithm is reliably initialized using an input-output system identification method described by Steiglitz-McBride. This method can be applicable to a class of discrete-time systems that includes the discrete K-FADS model. This V-MBF algorithm was evaluated subjectively and objectively through experiments conducted using synthetic data and found to be reliable in considered test scenarios. Accordingly, the method disclosed herein is feasible for determining physiologically meaningful estimates of absolute MBF.

The initial model is a continuous-rime K-FADS model from which a discrete-time K-FADS model can be obtained by applying a bilinear transform to the continuous-time K-FADS model. It should be noted that there is a simple relationship between the discrete-time and continuous-time K-FADS parameters. Using a systems theory framework, the problem of estimating the discrete-time K-FADS parameters is related to the problem of identifying a discrete-time system from given input and output data (i.e., input-output system identification). The V-MBF algorithm iteratively estimates the MBF for each voxel in the myocardium. The V-MBF algorithm can be initialized using an input-output system identification method, such as one described by Steiglitz-McBride, which is applicable to a class of discrete-time systems that includes the discrete K-FADS model. Each of these aspects will be described in turn with respect to a first approach to estimating the MBF for voxels of the cardiac system.

Continuous-Time K-FADS Model

For convenience, the RV factor, LV factor (i.e., Cp), Cu, and Cb can be denoted by the continuous-time functions $f_1(t)$, $f_2(t)$, $f_{1,3}(t)$, and $f_{i,4}(t)$, respectively, where i is the voxel index. With this notation it follows that $f_1$ and $f_2$ represent the activity concentration of the ammonia in the right ventricle and left ventricle, respectively. Additionally, $f_{i,3}(t)$, and $f_{i,4}(t)$ represent the activity concentration of free and trapped ammonia in myocardial tissue, respectively. It can be seen that it is assumed that the RV (right ventrical) and LV (left ventrical) factors are spatially constant (i.e., RV and LV factor are voxel independent). In the continuous-time K-FADS model the LV factor is modeled as a time shifted and dispersed function of the RV factor $$f_2(t) = \gamma f_1(t) * \exp(-\beta(t-\tau))u(t-\tau) \quad (4)$$

where $\gamma$, $\beta$, and $\tau$ (tau) are the unknown gain, time constant, and delay of the LV, respectively. Specifically, $\tau$ (tau) accounts for the fact that the ammonia activity first appears in the right ventricle and then, after a period of time, appears in the LV. The function u is the unit step function, and the notation * denotes the continuous-time convolution operator. The model for the LV factor in (4) can be motivated by observations of "isolated" RV and LV factors obtained from dynamic PET sequences and, in part, by the need for mathematical tractability. For example, consider if parameters $k_1$, $k_2$, and $k_3$ are pixel dependent and voxel i lies in the myocardium, then, applying the Laplace transform to (3) can lead to the following expressions for the activity concentration of the free and trapped ammonia in voxel i $$f_{i,3}(t) = k_{i,1} f_2(t) * \exp(-(k_{i,2} + k_{i,3})t) u(t) \quad (5)$$

$$f_{i,4}(t) = k_{i,3} f_{i,3}(t) * u(t) \quad (6)$$

It is noted that $k_{1,1}, k_{2,1}, \ldots, k_{I,1}$ are the preferred MBF parameters. In keeping with the assumptions behind (1), the activity for the ith pixel can be expressed as $$a_i(t) = c_{i,1} f_1(t) + c_{i,2} f_2(t) + c_{i,3} f_{i,3}(t) + c_{i,4} f_{i,4}(t) \quad (7)$$

The first term in (7) can be identified as the amount of spillover from the right ventricle, and the second term can be a combination of the ammonia activity in blood vessels within the myocardium and spillover from the left ventricle. More specifically, the constant $c_{i,1}$ accounts for the amount of the measured radioactivity in voxel in the case of a PET scan that is due to the blood plasma in the RV. Further, the constant $c_{i,2}$ accounts for the amount of the measured radioactivity in voxel i that is due to blood plasma in the LV (i.e., LV spill over) and blood plasma in the blood vessels of the myocardium. For this approach, it is assumed that $c_{i,2} = 0.05$. The third and fourth terms in (7) are the activity of the free and trapped ammonia in the myocardial tissue, respectively. The coefficients $c_{i,3}$ and $c_{i,4}$ represent the fractional volume of voxel i that can be occupied by the radiotracer in either the free or trapped states. Given the free space for water in myocardial tissue is approximately 80 percent, it is assumed that $c_{i,3} = c_{i,4} = 0.8$.

Within the descriptions herein, it can be convenient to let $f(t) = f_1(t)$ and $c_i = c_{i,1}$. From equations (4), (5), (6), and straightforward calculations, the functions $f_{i,3}(t)$ and $f_{i,4}(t)$ can be written as:

$$k_i = k_{i,2} + k_{i,3} \quad (8)$$

$$f_{i,3}(t) = -f(t) * [\exp(-\beta(t-\tau)) - \exp(-k_i(t-\tau))] u(t-\tau) \quad (9)$$

$$f_{i,4}(t) = \quad (10)$$
$$\gamma k_{i,1} k_{i,3} f(t) * \left[ \frac{\exp(-\beta(t-\tau))}{\beta(\beta - k_i)} - \frac{\exp(-k_i(t-\tau))}{k_i(\beta - k_i)} + \frac{1}{\beta k_i} \right] u(t-\tau)$$

By substituting these equations into (7) it can be shown that $$a_i(t) = c_i f(t) + \quad (11)$$
$$f(t) * [b_{i,1} + b_{i,2} \exp(-\beta(t-\tau)) + b_{i,3} \exp(-k_i(t-\tau))] u(t-\tau),$$
where $$b_{i,1} \triangleq \frac{\gamma c_{i,4} k_{i,1} k_{i,3}}{\beta k_i} \quad (12)$$

$$b_{i,2} \triangleq \gamma \left( c_{i,2} - \frac{c_{i,3} k_{i,1}}{\beta - k_i} + \frac{c_{i,4} k_{i,1} k_{i,3}}{\beta(\beta - k_i)} \right) \quad (13)$$

$$b_{i,3} \triangleq \frac{\gamma k_{i,1}}{\beta - k_i} \left( c_{i,3} - \frac{c_{i,4} k_{i,3}}{k_i} \right) \quad (14)$$

It can also be shown from straightforward calculations that $$k_{i,1} = \frac{c_{i,2}}{c_{i,3}} \frac{(\beta - k_i) b_{i,3} + \beta b_{i,1}}{b_{i,1} + b_{i,2} + b_{i,3}}. \quad (15)$$

Thus, given estimates for the parameters $\beta$, $\{k_i\}$, $\{c_i\}$, $\{b_{i,1}\}$, $\{b_{i,2}\}$, and $\{b_{i,3}\}$, and using the assumed values for $\{c_{i,2}\}$ and $\{c_{i,3}\}$, the MBF parameters $\{k_{i,1}\}$ can be estimated from equations (15). As stated above, it is assumed that $c_{i,2}=0.05$ and $c_{i,3}=0.8$ for all i.

Discrete-Time K-FADS Model

The next aspect of this approach is to address the problem of estimating the parameters $\beta$, $\{k_i\}$, $\{c_i\}$, $\{b_{i,1}\}$, $\{b_{i,2}\}$, and $\{b_{i,3}\}$ from discrete-time Time Activity Curve (TAC) data because continuous-time TAC data is not available in practice.

In practice, only samples of the TACs are available so let $y_i[n]$, i=1, 2, ..., I and x[n] denote the discrete-time signals obtained by sampling the ith TAC $a_i(t)$ and RV factor respectively $$y_i[n] \stackrel{\Delta}{=} a_i(nT), n=0,1,\ldots,N-1 \qquad (16)$$

$$x[n] \stackrel{\Delta}{=} f(nT), n=0,1,\ldots,N-1, \qquad (17)$$

where $f_s \stackrel{\Delta}{=} 1/T$ is the sampling rate and T is the sampling interval. It is noted that in applications where scan durations for dynamic sequence PET protocols are not uniform, the assumption that the TACs are sampled uniformly is inappropriate. However, uniform samples of the TACs can be obtained from non-uniform samples of the TACs via a suitable interpolation. It follows that, in order to estimate the MBF parameters, the parameters $\beta$, $\{k_i\}$, $\{c_i\}$, $\{b_{i,1}\}$, $\{b_{i,2}\}$, and $\{b_{i,3}\}$ are estimated from the data $y_i[n]$, n=0, 1, ..., N-1. It can be observed that the parameters $\{c_i\}$ are really nuisance parameters because they do not show up in the expression for $k_{i,1}$ (see equation (15)).

It is of interest to determine a discrete-time system with the property that its response to the discrete-time RV factor x[n] closely approximates the ith discrete-time TAC $y_i[n]$. The bilinear transformation is a way to transform a linear time-invariant continuous-time system into a linear time-invariant discrete-time system. A limitation of the bilinear transform is that a delay in a continuous-time system must be an integer multiple of the sampling interval. Taking the Laplace transform of (11), we get the following relationship $$A_i(s) = c_i F(s) + F(s)\left(b_{i,1}\frac{1}{s} + b_{i,2}\frac{1}{s+\beta} + b_{i,3}\frac{1}{s+k_i}\right)\exp(-s\tau), \qquad (18)$$
$$i = 1, 2, \ldots, I$$

As a result, it follows that the system function of the overall continuous-time system is given by $$H_{i,tot}(s) \stackrel{\Delta}{=} \frac{A_i(s)}{F(s)} = c_i + \left(b_{i,1}\frac{1}{s} + b_{i,2}\frac{1}{s+\beta} + b_{i,3}\frac{1}{s+k_i}\right)\exp(-s\tau) \qquad (19)$$

Assuming the delay T is a multiple of the sampling interval T, the system function of the desired discrete-time system, $H_i(z)$, can be obtained by applying the bilinear transformation to the overall continuous-time system $H_{i,tot}(s)$ $$H_i(z) = c_i + \left(\left[b_{i,1}\frac{1}{s} + b_{i,2}\frac{1}{s+\beta} + b_{i,3}\frac{1}{s+k_i}\right]\bigg|_{s=\frac{2}{T}\frac{1-s^{-1}}{1+s^{-1}}}\right)z^{-d} \qquad (20)$$

$$= c_i + \left(b'_{i,1}\frac{1+z^{-1}}{1-r_1 z^{-1}} + b'_{i,2}\frac{1+z^{-1}}{1-r_2 z^{-1}} + b'_{i,3}\frac{1+z^{-1}}{1-r_{i,3} z^{-1}} + \right)z^{-d} \qquad (21)$$

where $\tau=dT$ for some integer d, $r_1=1$, $r_2=(2/T+\beta)^{-1}(2/T-\beta)$, $r_{i,3}=(2/T+k_i)^{-1}(2/T-k_i)$, $b'_{i,1}=b_{i,1}(2/T)^{-1}$, $b'_{i,2}=b_{i,2}(2/T+\beta)^{-1}$, and $b'_{i,3}=b_{i,3}(2/T+k_i)^{-1}$.

It is noted that for this approach, the z-transform is used. Here let g[n] be an arbitrary discrete-time sequence. The z-transform g[n] can be defined as $$G(z) = \sum_{n=-\infty}^{\infty} g[n] z^{-n}.$$

It should be noted that the delay term (i.e., $Z^{-d}$ term) in equation (21) follows from the τ second delay in the continuous-time K-FADS model, which is the delay between activity appearing in the right and left ventricles.

As known in the art, the bilinear transformation has the property that it maps a stable continuous-time system into a stable discrete-time system. Moreover, the bilinear transformation avoids the problem of aliasing by mapping the jΩ axis into the unit circle of the complex plane. However, "frequency warping" can occur as a result of mapping the entire jΩ axis into the unit circle. Note, the frequency warping problem can be ameliorated by choosing a sufficiently high sampling rate $f_s$.

It follows from the definition in equation (21) that the discrete-time K-FADS model for the ith TAC can be represented by the following input-output relationship $$Y_i(z) = X(z) H_i(z; d, r_2, r_{i,3}, \theta_i) = \qquad (22)$$
$$c_i X(z) + X(z)\left[b'_{i,1}\frac{1+z^{-1}}{1-r_1 z^{-1}} + b'_{i,2}\frac{1+z^{-1}}{1-r_2 z^{-1}} + b'_{i,3}\frac{1+z^{-1}}{1-r_3 z^{-1}}\right]z^{-d}$$

where $\theta_i \stackrel{\Delta}{=} [b'_{i,1}, b'_{i,2}, b'_{i,3}, c_i]$ (recall $r_i=1$). The notation $H_i(z; d, r_2, r_{i,3}, \theta_i)$ explicitly illustrates the dependence of the ith system function on the unknown parameters. For the discussion below, it is beneficial to define the following notation:

$$\theta_{r_3} \stackrel{\Delta}{=} [r_{1,3}, r_{2,3}, \ldots, r_{I,3}]$$

$$\theta_{b'} \stackrel{\Delta}{=} [b'_{1,1}, b'_{2,1}, \ldots, b'_{I,1}, b'_{1,2}, b'_{2,2}, \ldots, b'_{I,2}, b'_{1,3}, b'_{2,3}, \ldots, b'_{I,3}]$$

$$c \stackrel{\Delta}{=} [c_1, c_2, \ldots, c_I]. \qquad (23)$$

The problem of interest is to estimate parameters of the discrete-time K-FADS model from the sampled TACs $y_i[n]$, I=1, 2, ..., I. Therefore, the V-MBF algorithm of this approach solves the following least-squares problem $$(P)\ (\hat{x}, \hat{d}, \hat{r}_2, \hat{\theta}_{r_3}, \hat{\theta}_{b'}, \hat{c}) = \arg\min_{x \geq 0, \theta \in S_\theta} \phi(x, d, r_2, \theta_{r_3}, \theta_{b'}, c), \qquad (24)$$

where $$\phi(x, d, r_2, \theta_{r_3}, \theta_{b'}, c) \stackrel{\Delta}{=} \sum_{i=1}^{I}\sum_{n=1}^{N}(y_i[n] - x[n] * h_i[n; d, r_2, r_{i,3}, \theta_i])^2 \qquad (25)$$

$$\theta \stackrel{\Delta}{=} [d, r_2, \theta_{r_3}, \theta_{b'}, c]. \qquad (26)$$

Additionally, $S_\theta$ is a feasible set of the parameters θ and $h_i[n; d, r_2, r_{i,3}, \theta_i]$ is the inverse Z-transform of $H_i(z; d, r_2, r_{i,3}, \theta_i)$.

In the development of the V-MBF algorithm, the problem (P) is simplified by assuming that the discrete-time d delay is known. Next, this assumption is removed by estimating the parameter d along with the other parameters of the discretetime K-FADS model. An initialization method is applied that exploits the well known Steiglitz-McBride algorithm.

A. Discrete-Time Delay Known

To minimize the objective function $\phi$ in (24), an algorithm is developed based on the group coordinate-descent method. By use of the term group coordinate-descent method it is understood that, in a cyclic fashion, the objective function $\phi$ is minimized with respect to a set of parameters while the other parameters are fixed.

Let $d_0$ denote the known discrete-time delay. Given initial estimates, $x^{(0)}, r_2^{(0)}, \theta_{r_3}^{(0)}, \theta_{b'}^{(0)}, c^{(0)}$ an algorithm for solving (P) proceeds as follows:

For $m = 0, 1, \ldots,$ (27)
$M - 1$ or repeat until some chosen criterion is met:

Step 1 $x^{(m+1)} = \mathrm{argmin}_{x \geq 0} \phi(x, d_0, r_2^{(m)}, \theta_{r_3}^{(m)}, \theta_{b'}^{(m)}, c^{(m)})$ Step 2 $(r_2^{(m+1)}, \theta_{r_3}^{(m+1)}) = \arg\min_{0 < r_2, \theta_{r_3} < 1} \phi(x^{(m+1)}, d_0, r_2, \theta_{r_3}, \theta_{b'}^{(m)}, c^{(m)})$ Step 3 $(\theta_{b'}^{(m+1)}, c^{(m+1)}) = \arg\min_{0 \leq c \leq 1} \phi(x^{(m+1)}, d_0, r_2^{(m+1)}, \theta_{r_3}^{(m+1)}, \theta_{b'}, c)$ (28)

end

Solution to Step 1 of the V-MBF Algorithm with Known Delay

In the solution to Step 1 of the V-MBF algorithm with known delay d, it is convenient to denote the next estimate for the RV factor as $\bar{x} \triangleq x^{(m+1)}$. Given its simplicity, the coordinate descent algorithm is used to iteratively determine $\bar{x}$. Let $e_1, e_2, \ldots, e_N$ be the search directions, where $e_j$ is an N×1 vector of zeros except for a 1 at the jth position. The steps of the coordinate descent algorithm for determining the update $x^{(m+1)}$ are as follows: Let $z_1 = x^{(m)}, \bar{x}^{(0)} = x^{(m)}, j=1,$ and $l=0$, and choose $\epsilon > 0$ Step 1.1 Determine $$\lambda_j = \arg\min_{\lambda} \phi(z_j + \lambda e_j), d_0, r_2^{(m)}, \theta_{r_3}^{(m)}, \theta_{b'}^{(m)}, c^{(m)})$$

Step 1.2 Let $z_{j+1} = z_j + \lambda_j e_j$. If jth component of $z_{j+1}$ is negative, then this value is set to zero. Note, this operation accounts for the nornegativity constraint of the discrete-time RV factor. If j<N, then increment j and repeat Step 1.1. Otherwise, if j=N, then go to Step 1.3.

Step 1.3 Let $\bar{x}^{(l+1)} = z_{N+1}$. If $\|\bar{x}^{(l+1)} - \bar{x}^{(l)}\| < \epsilon$ (or a specified number of desired iterations is reached), then stop and let $x_{(m+1)} = \bar{x}^{(l+1)}$. Else, let $z_1 \triangleq \bar{x}^{(l+1)}$ and j=1, increment l, and go to Step 1.1. Note, the step size $\lambda_j$ has a closed form expression.

Solution to Step 2 of the V-MBF Algorithm with Known Delay

Again, the simplicity of the coordinate descent method is exploited to compute a solution to the problem in Step 2. However, the coordinate descent method is expressed in a manner that is more convenient for this problem:
repeat until $$\|\theta_r^{(m+1)} - \theta_r^{(m)}\| < \epsilon \text{ where } \theta_r^{(m)} \triangleq [r_2^{(m)}, r_{1,3}^{(m)}, r_{2,3}^{(m)}, \ldots, r_{I,3}^{(m)}]$$ (29)

Step 2.1: $r_2^{(m+1)} = \arg\min_{0 < r_2 < 1} \phi(x^{(m+1)}, d_0, r_2, \theta_{r_3}^{(m)}, \theta_{b'}^{(m)}, c^{(m)})$ Step 2.2: for $i = 1, 2, \ldots, I,$ $$r_{i,3}^{(m+1)} = \arg\min_{0 < r_3 < 1} \sum_{n=1}^{N} (y_i[n] - x^{(m+1)}[n] * h_i[n; d, r_2^{(m+1)}, r_3, \theta_i^{(m+1)}])^2$$

end end

It should be observed that in Step 2.2 advantage is taken of the fact that the objective function $\phi$ is de-coupled in terms of the parameters $r_{1,3}, r_{2,3}, \ldots, r_{I,3}$. Also, a 1-D line search algorithm such as the golden section method can be used to solve the 1D minimization problems in Steps 2.1 and 2.2.

Solution to Step 3 of the V-MBF Algorithm with Known Delay

Referring to equation (25), it follows that the problem in equation (28) is equivalent to the following problems, i=1, 2, \ldots, I, $$\theta_i^{(m+1)} = \arg\min_{0 \leq c_i \leq 1} \min_{b'_{i,1}, b'_{i,2}, b'_{i,3}} \sum_{n=1}^{N} \left( \begin{array}{c} y_i[n] - c_i x^{(m+1)}[n] - b'_{i,1} w_1^{(m+1)}[n] - \\ b'_{i,2} w_2^{(m+1)}[n] - b'_{i,3} w_3^{(m+1)}[n] \end{array} \right)^2$$ (30)

where, $w_p^{(m+1)}[n], p = 1, 2,$ is the inverse Z-transform of (31)

$$W_p^{(m+1)}(z) = X^{(m+1)}(z) \frac{1 + z^{-1} z^{-d}}{1 - r_p z^{-1}}, p = 1, 2,$$

and $w_{i,3}^{(m+1)}[n]$ is the inverse Z-transform of (32)

$$W_{i,3}^{(m+1)}(z) = X^{(m+1)}(z) \frac{1 + z^{-1} z^{-d}}{1 - r_{i,3}^{(m+1)} z^{-1}}.$$

An optimization problem in equation (30) is a linear least-squares problem under the constraint $0 \leq c_i \leq 1$. If the constraint on $c_i$ ignored, then the update $\theta_i^{(m+1)}$ could be computed by solving the normal equations associated with the least-squares objective function in (30). Thus, if the solution to an unconstrained version of the least-squares problem in (30) is such that $0 \leq c_i^{(m+1)} \leq 1$ for all i, then no other steps should be necessary. Alternatively, if without loss of generality, the constraint is not satisfied for $i = i_0$, then additional steps should be taken. A straightforward strategy could be to first compute the updates $b'_{i_0,1}^{(m+1)}, b'_{i_0,2}^{(m+1)},$ and $b'_{i_0,3}^{(m+1)}$ by solving the normal equations associated with the following least-squares problem $$(b'^{(m+1)}_{i_0,1}, b'^{(m-1-\pi)}_{i_0,2}, b'^{(m+1)}_{i_0,3}) =$$ (33)

$$\mathrm{argmin}_{b'_{i_0,1}, b'_{i_0,2}, b'_{i_0,3}} \sum_{n=1}^{N} \left( \begin{array}{c} y_{i_0}[n] - c_{i_0}^{(m)} x^{(m+1)}[n] - b'_{i_0,1} w_1^{(m+1)}[n] \\ - b'_{i_0,2} w_2^{(m+1)}[n] - b'_{i_0,3} w_3^{(m+1)}[n] \end{array} \right)^2$$

The update $c_{i_0}^{(m+1)}$ could then be computed using the coordinate descent method $$c_{i_0}^{(m+1)} = \arg\min_{0 \leq c \leq 1} \Sigma_{n=1}^{N} (y_{i_0}[n] - c x^{(m+1)}[n] - b'^{(m+1)}_{i_0,1} w_1^{(m+1)}[n] - b'^{(m+1)}_{i_0,2} w_2^{(m+1)}[n] - b'^{(m+1)}_{i_0,3} w_{i_0,3}^{(m+1)}[n])^2$$ (34)

Iterating between equations (33) and (34) may lead to improved estimates for $c_{i_0}, b'_{i_0,1}, b'_{i_0,2},$ and $b'_{i_0,3}$.

Discrete-Time Delay Unknown

In the example above, the discrete-time delay d was assumed as known. Nevertheless, in practice it must be estimated. Let the integers $d_{min}$ and $d_{max}$ be the assumed minimum and maximum values for d. Then, the complete V-MBF algorithm follows for $d=d_{min}, \ldots, d_{max}$.

1. minimize $\phi(x, d, r_2, \theta_{r_3}, \theta_b, c)$ using the algorithm in the V-MBF algorithm assuming known discrete-time delay section within Section A (i.e., V-MBF algorithm assuming know descretime-time delay)
2. Store parameter estimates and value of least-squares objective function end The preferred estimates for the K-FADS parameters in this approach produce the smallest least-square error. The estimates for the MBF parameters are obtained using equation (15) and the estimates:

$$\hat{\beta} = \frac{2}{T} \frac{1-\hat{r}_2}{1+\hat{r}_2} \quad (35)$$

$$\hat{k}_i = \frac{2}{T} \frac{1-\hat{r}_{i,3}}{1+\hat{r}_{i,3}} \quad (36)$$

$$\hat{b}_{i,1} = \hat{b}'_{i,1} \frac{2}{T} \quad (37)$$

$$\hat{b}_{i,2} = \hat{b}'_{i,2}\left(\frac{2}{T} + \hat{\beta}\right) \quad (38)$$

$$\hat{b}_{i,3} = \hat{b}'_{i,3}\left(\frac{2}{T} + \hat{k}_i\right), \quad (39)$$

and the assumed values $c_{i,2}=0.05$ and $c_{i,3}=0.8$ for all i.

Initialization Procedure

To start the V-MBF algorithm, initial estimates for the RV factor x, $r_2$, and $\theta_{r_3}$ needed. One method for obtaining an initial estimate for the RV factor $x^{(0)}$ is for a user selected TAC of a voxel to be used that can essentially remain in the right ventricle throughout the duration of the scan. To generate initial estimates for $r_2$, and $\theta_{r_3}$, the known Steiglitz-McBride algorithm may be used.

To develop a method for computing an initial estimate, first observations can be used from equation (22) that for some 3rd-order polynomial $Q_i(z)$ and 2nd-order polynomial $P'_i(z)$, the z-transform of the ith TAC, is given by $$Y_i(z) = c_i X(z) + X(z) \frac{P'_i(z)(1+z^{-1})}{Q_i(z)} z^{-d}, i=1, 2, \ldots, I, \quad (40)$$

where the roots of $Q_i(z)$ are $r_1$, $r_2$, and $r_{i,3}$. Alternatively, for some polynomial $P'_i(z)$, equation (40) can be written as $$Y_i(z) = X(z) \frac{P_i(z)}{Q_i(z)}, i=1, 2, \ldots, I, \quad (41)$$

where the unknown numerator polynomial is of the form $P_i(z)=p_{i,0}+p_{i,1}z^{-1}+p_{i,2}z^{-2}+p_{i,3}z^{-3}+p_{i,d}z^{-d}+p_{i,d+1}z^{-(d+1)}+p_{i,d+2}z^{-(d+2)}+p_{i,d+3}z^{-(d+3)}$ because $P_i(z)=c_iQ_i(z)+P'_i(z)(1+z^{-1})z^{-d}$. In other words, each TAC is the output of an autoregressive moving-average (ARMA) model known in the art that is driven by the RV factor x[n].

Given an input-output pair for a linear, time-invariant system modeled as an ARMA model, the Steiglitz-McBride algorithm can provide estimates for ARMA parameters.

Thus, given a TAC, $y_i[n]$, and initial RV factor $x^{(0)}$, the Steiglitz-McBride algorithm can be used, which is an iterative algorithm, to estimate $P_i(z)$ and $Q_i(z)$. The Steiglitz-McBride algorithm can be summarized below $$(p_i^{(m+1)}, q_i^{(m+1)}) = \quad (42)$$

$$\underset{p,q}{\operatorname{argmin}} \frac{1}{2\pi} \int_{-\pi}^{\pi} \left| \frac{Y_i(e^{j\omega})Q(e^{j\omega})}{Q_i^{(m)}(e^{j\omega})} - \frac{X^{(0)}(e^{j\omega})P(e^{j\omega})}{Q_i^{(m)}(e^{j\omega})} \right|^2 d\omega,$$

where the discrete-time Fourier transform is used to obtain:

$$Y_i(e^{j\omega}) = \sum_{k=0}^{N-1} y_i[k] e^{-j\omega k} \quad (43)$$

$$X^{(0)}(e^{j\omega}) = \sum_{k=0}^{N-1} x^{(0)}[k] e^{-j\omega k} \quad (44)$$

$$P(e^{j\omega}) = \sum_{k=0}^{3} p_k e^{-j\omega k} + \sum_{k=0}^{3} p_{d+k} e^{-j\omega k} \quad (45)$$

$$Q(e^{j\omega}) = 1 + \sum_{k=1}^{3} q_k e^{-j\omega k} \quad (46)$$

$$p = [p_0, p_1, p_2, p_3, p_d, p_{d+1}, p_{d+2}, p_{d+3}] \quad (47)$$

$$q = [q_1, q_2, q_3]. \quad (48)$$

Also $P_i^{(m)}(e^{j\omega})$, $Q_i^{(m)}(e^{j\omega})$, $p_i^{(m+1)}$, and $q_i^{(m+1)}$ can be similarly defined, and) $Q_i^{(0)}(e^{j\omega})=1$ is the chosen initial estimate for $Q(e^{j\omega})$. Note, from Parseval's theorem, the objective function in (42) can be equivalent to a linear least-squares objective function. Thus, at the mth iteration, the Steiglitz-McBride algorithm entails a filtering step (i.e., initial RV factor $x^{(0)}[n]$ and ith TAC, $y_i[n]$, are filtered by $1/Q_i^{(m)}(z)$) and minimization of a linear least-squares objective function.

Let $\hat{Q}_i(z)$ denote the resulting estimate for $Q_i(z)$ using the Steiglitz-McBride algorithm and $z_{i,1} \geq z_{i,2} \geq z_{i,3}$ the roots of $\hat{Q}_i(z)$. The estimates for $r_2$ and $r_{i,3}$ are obtained from the roots of $\hat{Q}_i(z)$, I=1, 2, . . . , I, in the following manner. Because $\beta<1$ and $\beta>k_i$ by an order of magnitude and one of the roots of $Q_i(z)$ equals one, in theory, the initial estimates for the parameters $r_2$ and $r_{i,3}$ can be $r_2^{(0)}=\operatorname{avg}\{z_{1,2}, z_{2,2}, \ldots, z_{I,2}\}$ and $r_{i,3}^{(0)}=z_{i,3}$, respectively.

The Steiglitz-McBride algorithm is not used instead of the V-MBF algorithm to estimate the discrete-time K-FADS parameters when given an estimate for the RV factor because, for one reason, the roots of $\hat{Q}_i(z)$ are not guaranteed to be real with one root constrained to equal one, as required by the discrete K-FADS model. Another reason is that simulations discovered that estimating c and $\theta_{b'}$ from the estimates $\hat{P}_i(z)$, $\hat{Q}_i(z)$, i=1, 2, . . . , I, was not reliable.

Simulation Studies

To assess the potential of the V-MBF algorithm, simulated data was applied that modeled patient data used for cardiac health assessments. The model for the RV curve was $$f(t)=A(t-t_0)\exp(-\alpha(t-t_0))u(t-t_0), \quad (49)$$

where A=2700, $t_0$=14 seconds, and $\alpha$=0.12. Referring to equations (4), (5), (6), and (7), the parameters of the simulated data were $\gamma$=0.2, $\beta$=0.1, $\tau$=13 seconds, and for all i, $k_{i,2}$=0.001 $s^{-1}$, $k_{i,3}$=0.01 $s^{-1}$, $c_i$=0.03, $c_{i,2}$=0.05, $c_{i,3}$=0.8, $c_{i,4}$=0.8. Note, the V-MBF algorithm does not require that the parameters $c_i$, $k_{i,2}$, and $k_{i,3}$ be voxel independent. The values for these parameters were simply chosen for exemplary purposes. The MBF parameters $\{k_{i,1}\}$ (units s$^{-1}$) for the 20 voxel scenario that were considered were $$k_1 = [0.0075, 0.0462, 0.0371, 0.0233, 0.0534, 0.0281,$$
$$0.0320, 0.0336, 0.0433, 0.0036, 0.0083, 0.0034,$$
$$0.0021, 0.0103, 0.0096, 0.0345, 0.0316, 0.0031,$$
$$0.0257, 0.0346]. \quad (50)$$

The simulated TACs $a_i(t)$, I=1, 2, ..., I were computed using equation (11) and the above parameter values.

To model the integration characteristic of the scanner, the simulated TACs were integrated using a time-varying window. The resulting integrated data simulated the activity data that would actually be available in practice. A typical protocol used at an exemplary PET Center could leads to the following specification for the simulated integrated TACs (I-TACs)

$$g_k = \begin{cases} \frac{1}{T_1} \int_{(k-1)T_1}^{kT_1} a_i(t)dt, k = 1, 2, \ldots, 20 \\ \frac{1}{T_2} \int_{(k-1)T_2}^{kT_2} a_i(t)dt, k = 21, 22, \ldots, 25 \\ \frac{1}{T_3} \int_{(k-1)T_3}^{kT_3} a_i(t)dt, k = 26, 27, \ldots, 31, \end{cases} \quad (51)$$

where $T_1$=3 seconds, $T_2$=12 seconds, and $T_3$=30 seconds.

The V-MBF algorithm can be based on standard TAC data (i.e., $a_i(nT)$). Consequently, the I-TAC data is preferrably pre-processed. The I-TAC data is assumed to be nearly piecewise linear. It follows using a known method from Kuhle that the standard TAC data at the midpoints of the windows is approximately:

$$a_i(0.5(kT_1+(k-1)T_1)) \approx g_k, k=1,2,\ldots,20 \quad (52)$$

$$a_i(0.5(kT_2+(k-1)T_2)) \approx g_k, k=21,22,\ldots,25 \quad (53)$$

$$a_i(0.5(kT_3+(k-1)T_3)) \approx g_k, k=26,27\ldots,31 \quad (54)$$

Now, standard sampled TAC data can be estimated from the measured activity data $\{g_k\}$ using interpolation. Specifically, the "known" values for $a_i(t)$, $\{a_i(0.5(kT_1+(k-1)T_1))\}_{k=1}^{20}$, $\{a_i(0.5(kT_2+(k-1)T_2))\}_{k=21}^{25}$, and $\{a_i(0.5(kT_3+(k-1)T_3))\}_{k=31}^{26}$ can be used (see equations (52), (53), and (54)), and linear interpolation to obtain estimates for $y_i[n]=a_i(nT)$, n=0, 1, ..., N−1. In the simulations, a preferred sampling interval is T=0.05 sec. It is noted that the approach described above for obtaining standard sampled TAC data would also be used to generate an initial RV factor from I-TAC data located in the RV.

Figure 2:
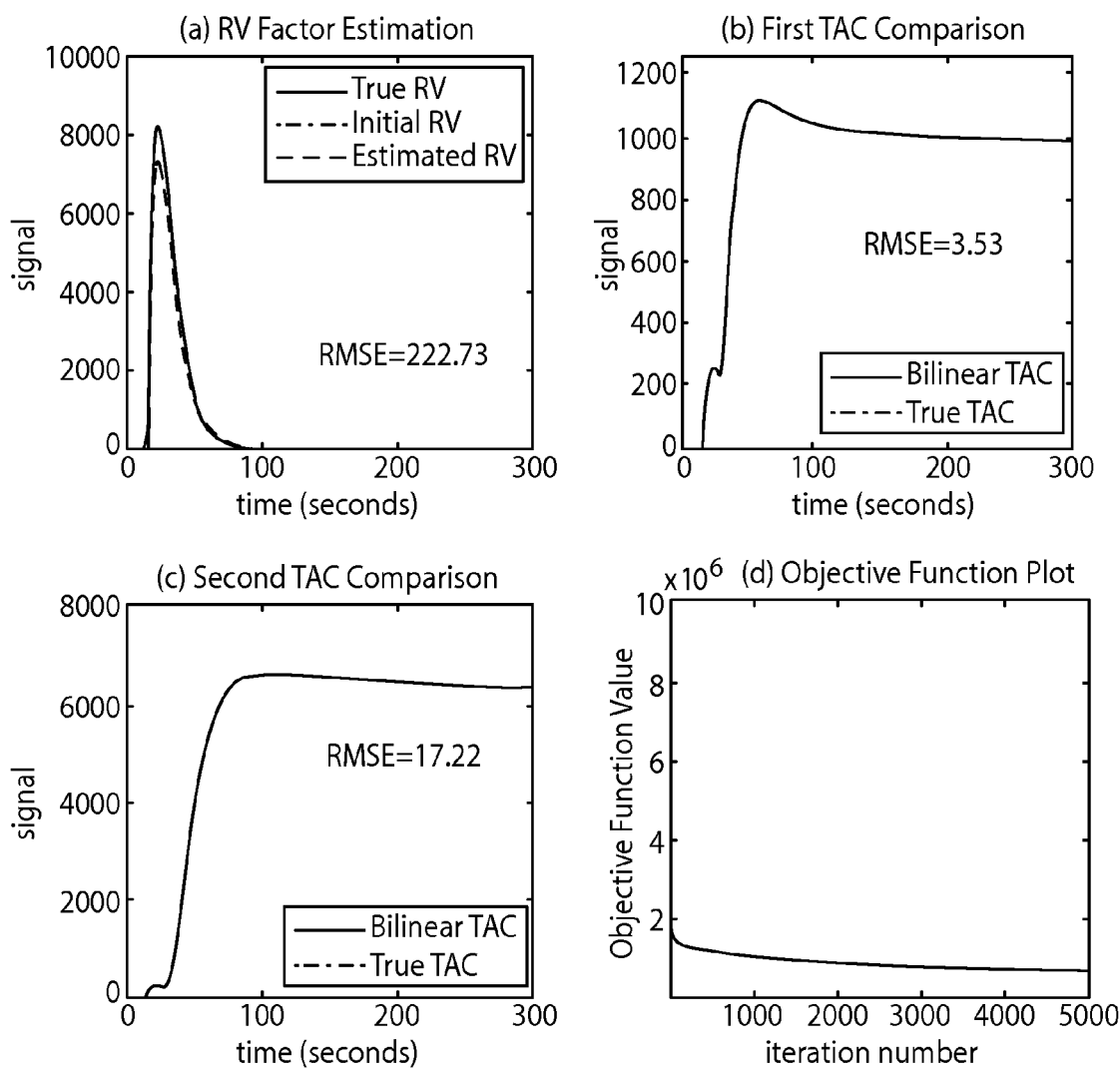
FIG. 2 illustrates results from a V-MBF algorithm applied to synthetic data: (a) true, initial, and estimated RV factor, (b) comparison of true TAC (computed analytically) and estimated TAC generated using the discrete-time K-FADS model and estimated parameters, (c) same as (b) except for a different TAC, and (4) least-squares objective function as a function of iteration number.

The V-MBF algorithm described above was applied for 5000 iterations where one sub-iteration was used to update the estimate for the RV curve. In this simulation, the maximum error in the MBF estimates was 1.5 percent. A typical result of a V-MBF algorithm is summarized in the FIG. 2, where (a) shows a true, initial, and estimated RV factor, (b) compares a true TAC (computed analytically) and with one generated using the discrete-time K-FADS model and estimated parameters, (c) is the same as (b) except for a different voxel, and (d) is a plot of the least-squares objective function as a function of iteration number. In the exemplary study, the V-MBF algorithm was stable and monotonically decreased the least-squares objective function (see FIG. 2(d)).

Thus, the V-MBF algorithm can be based on a model that accounts for the fact that the shape of TACs due to ischemic and normal tissue are different. In fact, the model can allow for the factors that represent free and trapped ammonia to be voxel dependent and physiologically appropriate. By contrast, in a standard FADS model, it is assumed that TACs in ischemic and normal tissue can be modeled as a linear combination of the same three factors. The present methods and systems represent a significant improvement in the art as a more appropriate model to provide more accurate MBF estimates than available methods.

The V-MBF algorithm presented herein performs well in simulation studies where unknown MBF parameters varied by an order of magnitude. This suggests that the V-MBF algorithm is robust and would perform well in practice, where MBF values due to ischemic and normal tissue can vary over a wide range. Although random noise was not added to the simulated TAC data, interpolation noise and noise due to the discretization of the continuous-time K-FADS model were present. Also, because only the integrated RV factor is available, the first time point where the RV factor is nonzero can never be known with certainty. With these three sources of noise, the maximum error of the MBF parameters estimates was 1.5 percent. It should be noted that including more data points should, lead to improved MBF estimates because the parameter β is voxel independent.

II. A Second Approach

A second approach to MBF analysis will be descibed as follows. For clarity, equations will be renumbered to start with equation (1) within the discussion of this other approach.

As discussed above, the problem of estimating the weights and signal vectors of the above described models is a blind inverse problem. In this case, the data are nonnegative J×1 vectors $\{a_1, a_2, \ldots, a_J\}$ that are modeled as a weighted sum of signal vectors plus noise $$a_i = \sum_{k=1}^{K} c_{ik} f_k + e_i, \quad i = 1, 2, \ldots, I \quad (1)$$

where the J×1 signal vectors, $\{f_k\}$, and signal weights, $\{c_{i,k}\}$, are nonnegative and unknown, and $\{e_i\}$ is the noise. In our discussion of this approach, it will be convenient to use an equivalent expression for the model $$a_{ij} = \sum_{k=1}^{K} c_{ik} f_{jk} + e_{ij}, \quad i = 1, 2, \ldots, I, j = 0, 1, 2, \ldots, J-1, \quad (2)$$

where $a_{ij}$ and $e_{ij}$ are the jth components of $a_i$ and $e_i$, respectively, and $f_{jk}$ is the jth value of the kth signal vector. An example where this model is used is cardiac imaging using dynamic positron emission tomography (PET), where $a_{ij}$ is a measure of the radiopharmaceutical concentration in the ith voxel at the jth time point. Another example is multispectral imaging, where $a_{ij}$ represent the value of the ith pixel in the jth spectral plane.

Given the data $\{a_{ij}\}$, the problem is to estimate the weights $\{c_{jk}\}$ and signal vector values $\{f_{jk}\}$. The least-squares estimates of the weights and signal vector values are obtained by minimizing the least-squares objective function L subject to a non-negativity constraint.

$$(\hat{c}, \hat{f}) = \arg \min_{c \geq 0, f \geq 0} L(c, f), \quad (3)$$

where $$L(c, f) = \sum_{i=1}^{I} \sum_{j=0}^{J-1} \left( a_{ij} - \sum_{k=1}^{K} c_{ik} f_{jk} \right)^2. \quad (4)$$

The vectors c and f contain the signal weights and signal vector values, respectively:

$$c \triangleq [c_{11}, c_{21}, \ldots, c_{I1}, c_{12}, c_{22}, \ldots, c_{I2}, \ldots, c_{1K}, c_{2K}, \ldots, c_{IK}] \quad (5)$$

$$f \triangleq [f_{11}, f_{21}, \ldots, f_{I1}, f_{12}, f_{22}, \ldots, f_{I2}, \ldots, f_{1K}, f_{2K}, \ldots, f_{IK}] \quad (6)$$

The least squares estimation problem is ill-posed, so the results are highly dependent on the initial estimates.

Estimation of Signal Vectors and Weights

A known standard least-squares algorithm by Lee and Seung monotonically decreased the least-squares objective function, L, and produced nonnegative estimates. In this section, this "standard least-squares algorithm" is re-derived using a known technique called the majorize-minimize method (MM). This derivation will place the proposed least-squares extensions in context so that their advantages over the standard least-squares algorithm are clear.

An approach for minimizing the least-squares objective function, L, would be, in an alternating fashion, to minimize L with respect to the signal weights while holding the signal vectors fixed to their current value, and then minimize L with respect to the signal vectors while holding the signal weights fixed to their current value. Given initial estimates $\{c_{ij}^{(0)}\}$ and $\{f_{jk}^{(0)}\}$, this algorithm can be expressed mathematically as follows:

Step 1' $c^{(n+1)} = \operatorname*{argmin}_{c \geq 0} L(c, f^{(n)})$

Step 2' $f^{(n+1)} = \operatorname*{argmin}_{f > 0} L(c^{(n+1)}, f)$

Step 3' Repeat Steps 1' and 2' for a fixed number of iterations or until some desired stopping criterion is met Here, Steps 1' and 2' imply that the resulting algorithm monotonically decreases the least-squares objective function $$L(c^{(n+1)}, f^{(n+1)}) \leq L(c^{(n)}, f^{(n)}) \text{ for all } n=0,1,2 \quad (7)$$

Introduction to the MM Method

The minimizations problems in Steps 1' and 2' are difficult so an alternative approach is needed. In this section, the MM method is introduced; then, the following section demonstrates how the MM method can be used to develop an algorithm that, by construction, monotonically decreases the least-squares objective function, produces nonnegative estimates, and is straightforward to implement.

Consider a real valued function $f$ with domain $D \in R^n$ that is to be minimized. A real valued function g with domain $\{(x_1, x_2): x_1, x_2 \in D\}$ is said to majorize the function $f$ if the following conditions hold for all x, y∈D:

$$g(x,y) \geq f(x) \quad (C1')$$

and $$g(x,x) = f(x). \quad (C2')$$

MM algorithms are a viable approach provided a majorizing function can be found that is easier to minimize than the original objective function. Assuming that g is a suitable majorizing function for f, the corresponding MM algorithm is $$x^{(k+1)} = \arg\min_{x \in D} g(x, x^{(k)}) \quad (8)$$

It follows from (C1') and (C2') that the MM algorithm defined by (8) is monotonic $$f(x^{(k+1)}) \leq g(x^{(k+1)}, x^{(k)}) \leq g(x^{(k)}, x^{(k)}) = f(x^{(k)}) \quad (9)$$

Standard Least-Squares Algorithm

The following describes an MM algorithm for estimating signal vectors and signal weights that is equivalent to the least-squares algorithm of Lee and Seung.

In the discussion that follows, it will be convenient to define sets $D_c$ and $D_f$, where $D_c$ and $D_f$ are the set of nonnegative vectors of dimension IK×1 and JK×1, respectively. Let $c_{(n)}$ and $f^{(n)}$ be the current estimates for the signal weights and signal vectors, respectively. Further, let q and r be certain majorizing functions that satisfy the following conditions for x, y, c∈$D_c$ and s, t, f∈$D_f$ be $$q(x,y,f) \geq L(x,f) \quad (C1)$$

$$q(x,x,f) = L(x,f) \quad (C2)$$

$$r(s,t,c) \geq L(c,s) \quad (C3)$$

$$r(x,x,c) = L(c,x). \quad (C4)$$

Using the idea behind equation (8), CLA put forth the following MM algorithm for minimizing the least-squares objective function L $$c^{(n+1)} = \operatorname*{argmin}_{c \geq 0} q(c, c^{(n)}, f^{(n)}) \quad (10)$$

$$f^{(n+1)} = \operatorname*{argmin}_{f \geq 0} r(f, f^{(n)}, c^{(n+1)}). \quad (11)$$

It is straightforward to show that least-squares objection function monotonically decreases with increasing iterations. First, from (C1) and equation (10) it follows, respectively that $$L(c^{(n+1)}, f^{(n)}) \leq q(c^{(n+1)}, c^{(n)}, f^{(n)}) \quad (12)$$

$$q(c^{(n+1)}, c^{(n)}, f^{(n)}) \leq q(c^{(n+1)}, c^{(n)}, f^{(n)}). \quad (13)$$

Similarly, from (C3) and equation (11) it follows, respectively, that $$L(c^{(n+1)}, f^{(n+1)}) \leq r(f^{(n+1)}, f^{(n)}, c^{(n+1)}) \quad (14)$$

$$r(f^{(n+1)}, f^{(n)}, c^{(n+1)}) \leq r(f^{(n+1)}, f^{(n)}, c^{(n+1)}) \quad (15)$$

Now, from (C2) and (C4) it follows, respectively, that $$q(C^{(n)}, c^{(n)}, f^{(n)}) = L(c^{(n)}, f^{(n)}) \quad (16)$$

$$r(f^{(n)}, f^{(n)}, c^{(n+1)}) = L(c^{(n+1)}, f^{(n)}). \quad (17)$$

Consequently, we can conclude from equations (12) (17) that $$L(c^{(n+1)}, f^{(n+1)}) \leq L(c^{(n)}, f^{(n)}). \quad (18)$$

At this point, all that remains is to determine the majorizing functions q and r. From equation (4), the least-squares objection function can be written as $$L(c, f) = \sum_{i=1}^{I} \sum_{j=0}^{J-1} \left[ a_{ij}^2 - 2a_{ij} \sum_{k=1}^{K} c_{ik} f_{jk} + \left( \sum_{k=1}^{K} c_{ik} f_{jk} \right)^2 \right]. \quad (19)$$

Using a known approach, the convexity of the square function is exploited to obtain the following inequality:

$$\left(\sum_{k=1}^{K} c_{ik}f_{jk}\right)^2 = \left(\sum_{k=1}^{K} \frac{c_{ik}^{(n)}f_{jk}}{\left[\sum_{k'=1}^{K'} c_{ik'}^{(n)}f_{jk'}\right]} \left[\frac{\left[\sum_{k'=1}^{K'} c_{ik'}^{(n)}f_{jk'}\right]c_{ik}}{c_{ik}^{(n)}}\right]\right)^2 \quad (20)$$

$$\leq \sum_{k=1}^{K} \frac{c_{ik}^{(n)}f_{jk}}{\left[\sum_{k'=1}^{K'} c_{ik'}^{(n)}f_{jk'}\right]} \left(\frac{\left[\sum_{k'=1}^{K'} c_{ik'}^{(n)}f_{jk'}\right]c_{ik}}{c_{ik}^{(n)}}\right)^2 \quad (21)$$

$$\leq \hat{a}_{ij}(c^{(n)}, f) \sum_{k=1}^{K} \left(\frac{c_{ik}^2}{c_{ik}^{(n)}}f_{jk}\right), \quad (22)$$

where $c^{(n)} \in D_c$, $f \in D_f$, and $$\hat{a}_{ij}(c, f) \triangleq \sum_{k=1}^{K} c_{ik}f_{jk}. \quad (23)$$

It should be noted that (20) is a convex combination with weights $w_{ijk} \triangleq c_{ik}^{(n)}f_{jk}f_{jk}[\Sigma_{k'=1}^{K'}c_{ik'}^{(n)}f_{jk'}]^{-1}$, where $w_{ijk} \geq 0$ and $\Sigma_{k=1}^{K} w_{ijk}=1$ for all i, j. Replacing the $(\Sigma_{k=1}^{K} c_{ik}f_{jk})^2$ term in (19) by the right hand side of (22), we get the following majorizing function for L $$q(c, c^{(n)}, f) \triangleq \quad (24)$$
$$\sum_{i=1}^{I}\sum_{j=0}^{J-1}\left\{a_{ij}^2 - 2a_{ij}\sum_{k=1}^{K}c_{ik}f_{jk} + \hat{a}_{ij}(c^{(n)}, f)\sum_{k=1}^{K}\left(\frac{c_{ik}^2}{c_{ik}^{(n)}}f_{jk}\right)\right\},$$

where, by construction, $q(c,c^{(n)},f) \geq L(c,f)$ and $q(c,c,f)=L(c,f)$ for all $c, c^{(n)} \in D_c$ and $f \in D_f$.

By repeating the steps used to derive equation (24) with the roles of c and f switched, the majorizing function $$r(f, f^{(n)}, c) \triangleq \quad (25)$$
$$\sum_{i=1}^{I}\sum_{j=0}^{J-1}\left\{a_{ij}^2 - 2a_{ij}\sum_{k=1}^{K}c_{ik}f_{jk} + \hat{a}_{ij}(c, f^{(n)})\sum_{k=1}^{K}\left(\frac{f_{jk}^2}{f_{jk}^{(n)}}c_{jk}\right)\right\},$$

which satisfies the properties $r(f,f^{(n)},c) \geq L(c,f)$ and $r(f,f,c)=L(c,f)$ for all $c \in D_c$ and $f, f^{(n)} \in D_f$.

To determine updates defined in equations (10) and (11), the partial derivatives of $q(c, c^{(n)}, f^{(n)})$ and $r(f, f^{(n)}, c^{(n+1)})$ are computed with respect to c and f, respectively, with the corresponding equations set to zero. It is straightforward to show that the derivatives are given by $$\frac{\partial q(c, c^{(n)}, f^{(n+1)})}{\partial c_{i'k'}} = \sum_{j=0}^{J-1}\left[-2a_{i'j}f_{jk'}^{(n)} + 2\frac{c_{i'k'}}{c_{i'k'}^{(n)}}f_{jk'}^{(n)}\hat{a}_{ij}(c^{(n)}, f^{(n)})\right] \quad (26)$$

$$\frac{\partial r(f, f^{(n)}, c^{(n+1)})}{\partial f_{j'k'}} = \sum_{i=0}^{I}\left[-2a_{ij'}c_{ik'}^{(n+1)} + 2\frac{f_{j'k'}}{f_{j'k'}^{(n)}}c_{ik'}^{(n+1)}\hat{a}_{ij}(c^{(n+1)}, f^{(n)})\right]. \quad (27)$$

Setting the derivatives in equations (26) and (27) to zero leads to the following least-squares algorithm for estimating the signal weights and signal vectors:

$$c_{ik}^{(n+1)} = c_{ik}^{(n)}\frac{\sum_{j=0}^{J-1}f_{jk}^{(n)}a_{ij}}{\sum_{j=0}^{J-1}f_{jk}^{(n)}\hat{a}_{ij}(c^{(n)}, f^{(n)})}, \quad (28)$$

$$i = 1, 2, \ldots, I, k = 1, 2, \ldots, K$$

$$f_{jk}^{(n+1)} = f_{jk}^{(n)}\frac{\sum_{i=0}^{I-1}c_{ik}^{(n+1)}a_{ij}}{\sum_{i=0}^{I-1}c_{ik}^{(n)}\hat{a}_{ij}(c^{(n+1)}, f^{(n)})}, \quad (29)$$

$$j = 0, 1, 2, \ldots, I, k = 1, 2, \ldots, K.$$

As shown above, the starting point for developing the proposed MM algorithm was equations (10) and (11). Alternatively, an MM algorithm can be developed by updating the signal vectors first and then the signal weights:

$$f^{(n+1)} = \arg\min_{f \geq 0} r(f, f^{(n)}, c^{(n)}) \quad (30)$$

$$c^{(n+1)} = \arg\min_{c \geq 0} q(c, c^{(n)}, f^{(n+1)}). \quad (31)$$

In this case, the resulting MM algorithm is $$f_{jk}^{(n+1)} = f_{jk}^{(n)}\frac{\sum_{i=1}^{I}c_{ik}^{(n)}a_{ij}}{\sum_{i=1}^{I}c_{ik}^{(n)}\hat{a}_{ij}(c^{(n)}, f^{(n)})}, \quad (32)$$

$$j = 0, 1, 2, \ldots, J, k = 1, 2, \ldots, K$$

$$c_{jk}^{(n+1)} = c_{jk}^{(n)}\frac{\sum_{j=1}^{J-1}f_{jk}^{(n+1)}a_{ij}}{\sum_{j=0}^{J-1}f_{jk}^{(n+1)}\hat{a}_{ij}(c^{(n)}, f^{(n+1)})}, \quad (33)$$

$$i = 0, 1, 2, \ldots, I, k = 1, 2, \ldots, K.$$

Additive Least-Squares Algorithm

The standard least-squares algorithm defined by equations (28) and (29) (see also (32) and (33)) is referred to as a multiplicative algorithm. In this section, we derive an additive algorithm by developing an alternative majorizing function for the least-squares objective function L.

Exploiting the convexity of the square function we obtain the following inequality $$\left(\sum_{k=1}^{K} c_{ik} f_{jk}\right)^2 = \left[\sum_{k=1}^{K} \frac{f_{jk}}{\bar{f}_j}(\bar{f}_j c_{ik} - \bar{f}_j c_{ik}^{(n)} + \hat{a}_{ij}(c^{(n)}, f))\right]^2 \quad (34)$$

$$\leq \sum_{k=1}^{K} \frac{f_{jk}}{\bar{f}_j}(\bar{f}_j c_{ik} - \bar{f}_j c_{ik}^{(n)} + \hat{a}_{ij}(c^{(n)}, f))^2 \quad (35)$$

where $\bar{f}_j \triangleq \sum_{k=1}^{K} f_{jk}$, $c^{(n)} \in D_c$, and $f \in D_f$. It should be noted that (34) is a convex combination with weights $w_{jk} \triangleq f_{jk}/\bar{f}_j$, where $w_{jk} \geq 0$ for all j,k and $\sum_{k=1}^{K} w_{jk}=1$ for all j. Replacing the $(\sum_{k=1}^{K} c_{ik}f_{jk})^2$ term in (19) by the right hand side of (35), we get the following majorizing function for L $$q_A(c, c^{(n)}, f) \triangleq \sum_{i=1}^{I} \sum_{j=0}^{J-1} \left\{ a_{ij}^2 - 2a_{ij} \sum_{k=1}^{K} c_{ik} f_{jk} + \sum_{k=1}^{K} \frac{f_{jk}^2}{f_{jk}^{(n)}}(\bar{f}_j c_{jk} - \bar{f}_j c_{ik}^{(n)} + \hat{a}_{ij}(c^{(n)}, f))^2 \right\}, \quad (36)$$

where, by construction, $q_A(c,c^{(n)},f) \geq L(c,f)$ and $q_A(c,c,f)=L(c,f)$ for all c, $c^{(n)} \in D_c$ and $f \in D_f$.

When the steps used to derive equation (24) are repeated with the roles of c and f switched, we get the following majorizing function:

$$r_A(f, f^{(n)}, c) \triangleq \sum_{i=1}^{I} \sum_{j=0}^{J-1} \left\{ a_{ij}^2 - 2a_{ij} \sum_{k=1}^{K} c_{ik} f_{jk} + \sum_{k=1}^{K} \frac{c_{ik}}{\bar{c}_i}(\bar{c}_i f_{jk} - \bar{c}_i f_{jk}^{(n)} + \hat{a}_{ij}(c, f^{(n)}))^2 \right\}, \quad (37)$$

which satisfies the properties, $r_A(f,f^{(n)},c) \geq L(c,f)$ and $r_A(f,f,c)=L(c,f)$ for all $c \in D_c$ and $f, f^{(n)} \in D_f$.

The updates defined by equations (10) and (11) are determined with q and r replaced by $q_A$ and $r_A$, respectively. Specifically, the partial derivatives of $q_A(c, c^{(n)}, f^{(n)})$ and $r_A(f, f^{(n)}, c^{(n+1)})$ are computed with respect to c and f, respectively, and then the resulting equations are set to zero. The desired derivatives can be given by $$\frac{\partial q_A(c, c^{(n)}, f^{(n)})}{\partial c_{i'k'}} = -2\sum_{j=0}^{J-1} a_{i'j} f_{jk'}^{(n)} + 2\sum_{j=0}^{J-1} \frac{f_{jk'}^{(n)}}{\bar{f}_j^{(n)}}[\bar{f}_j^{(n)} c_{i'k'} - \bar{f}_j^{(n)} c_{i'k'}^{(n)} + \hat{a}_{i'j}(c^{(n)}, f^{(n)})]\bar{f}_j^{(n)} \quad (38)$$

$$\frac{\partial r_A(f, f^{(n)}, c^{(n+1)})}{\partial f_{j'k'}} = -2\sum_{i=0}^{I} a_{ij'} f_{jk'}^{(n+1)} + 2\sum_{i=0}^{I-1} \frac{c_{ik'}^{(n+1)}}{\bar{c}_i^{(n+1)}}[\bar{c}_i^{(n+1)} f_{j'k'} - \bar{c}_i^{(n+1)} f_{j'k'}^{(n)} + \hat{a}_{ij'}(c^{(n+1)}, f^{(n)})]\bar{c}_i^{(n+1)} \quad (39)$$

Setting the derivatives in equations (38) and (39) to zero leads to the following additive least-squares algorithm for estimating the signal weights and signal vectors $$c_{ik}^{(n+1)} = \left[ c_{ik}^{(n)} + \frac{\sum_{j=0}^{J-1} f_{jk}^{(n)}[a_{ij} - \hat{a}_{ij}(c^{(n)}, f^{(n)})]}{\sum_{j=0}^{J-1} f_{jk}^{(n)} \bar{f}_j^{(n)}} \right]_+, \quad (40)$$

$$i = 1, 2, \ldots, I, \quad k = 1, 2, \ldots K$$

$$f_{jk}^{(n+1)} = \left[ f_{jk}^{(n)} + \frac{\sum_{i=1}^{I} c_{jk}^{(n+1)}[a_{ij} - \hat{a}_{ij}(c^{(n+1)}, f^{(n)})]}{\sum_{i=1}^{I} c_{ik}^{(n+1)} \bar{c}_i^{(n+1)}} \right]_+, \quad (41)$$

$$j = 0, 1, \ldots J-1, \quad k = 1, 2, \ldots, K,$$

where $[x]_+ \triangleq \max(0, x)$. Now, when the signal vectors are updated first and then the signal weights, the corresponding additive least-squares algorithm is given by $$f_{jk}^{(n+1)} = \left[ f_{jk}^{(n)} + \frac{\sum_{i=1}^{I} c_{ik}^{(n)}[a_{ij} - \hat{a}_{ij}(c^{(n)}, f^{(n)})]}{\sum_{i=1}^{I} c_{ik}^{(n)} \bar{c}_i^{(n)}} \right]_+, \quad (42)$$

$$j = 0, 1, \ldots, J-1, \quad k = 1, 2, \ldots, K,$$

$$c_{ik}^{(n+1)} = \left[ c_{ik}^{(n)} + \frac{\sum_{j=0}^{J-1} f_{jk}^{(n+1)}[a_{ij} - \hat{a}_{ij}(c^{(n)}, f^{(n+1)})]}{\sum_{j=0}^{J-1} f_{jk}^{(n+1)} \bar{f}_j^{(n+1)}} \right]_+, \quad (43)$$

$$i = 1, 2, \ldots, I, \quad k = 1, 2, \ldots, K.$$

Extensions of Standard Least-Squares Algorithm: Application to Myocardial Blood Flow Estimation Using Positron Emission Tomography In this section, the standard least-squares algorithm application to the problem of estimating absolute myocardial blow (MBF) noninvasively using positron emission tomography is addressed. Then, extensions of the standard least-squares algorithm are presented that lead to improved MBF estimates. These extensions are also applicable to the additive least-squares algorithm.

To assess the heart of a patient, it is desirable to estimate the patient's MBF noninvasively. One way to obtain this information is to first perform a dynamic PET scan of the patient's heart and then apply estimation algorithms that are based on equation (2) and other available models for dynamic cardiac PET data. Note, in the PET literature, the terms factor curves and factor weights are used for the terms signal vectors and signal weights. For PET based MBF estimation, the least-squares algorithm in equations (28) and (29) could first be used to estimate the factor curves and weights for a given dynamic PET data set. Then, using the resulting estimates, standard methods could be used to estimate the absolute myocardial blood flow of the patient. The accuracy of the MBF estimates would greatly depend on the performance of the standard least-squares algorithm, which, as mentioned previously, is highly dependent on the initial estimates. Therefore, we develop extensions of the least-squares method that greatly reduce the parameter space by incorporating a priori information. In practice, the proposed algorithms are expected to be more stable and produce more accurate estimates of the factor curves and weights than the standard least-squares algorithm. Therefore, improved MBF estimation is anticipated when the proposed algorithms are used instead of the standard least-squares algorithm.

Model

Let $a_i(t)$ denote the continuous-time activity in voxel i at time t, where $t \in [0, T]$ and T is the duration of the scan. In practice, only samples of the data are available so $a_{ij}$ denotes the activity in voxel i at time $t = jT_s$ (i.e., time frame j)

$$a_{ij} \triangleq a_i(jT_s), i=1,2,\ldots,I, j=0,1,2,\ldots,J-1 \quad (44)$$

where $T_s$ is the sampling interval, I is the number of voxels, and J is the number of time frames. Referring to equation (2), it is typically assumed that the activity $a_{ij}$ is a linear combination of K=3 unknown factor curves representing the sampled right ventricular blood pool, left ventricular blood pool, and myocardial tissue curves, respectively. Note, the factor weights for a particular time frame can be viewed as an image and therefore are collectively referred to as a factor image.

Physiological Based Constraints: Right and Left Ventricle Tissue Curves go to Zero Due to the physiology of the heart and half-life of the radiopharmaceuticals used in nuclear cardiology, the factor curves for the right and left ventricles go to zero as t approaches 0, which a priori information is incorporated into the estimation problem. Thus, an alternative to the least-squares formulation is to add a penalty term to the least-squares objective function that "forces" the factor curves for the right ventricle $f_1 \triangleq [f_{11}, f_{21}, \ldots, f_{J1}]$ and left ventricle $f_2 \triangleq [f_{12}, f_{22}, \ldots, f_{J2}]$ to go to zero. Given its potential advantage over the standard least-squares method, we propose the following penalized least-squares method $$(\hat{c}, \hat{f}) = \arg\min_{c \geq 0, f \geq 0} L(c, f) + \beta_1 \Lambda(f_1) + \beta_2 \Lambda(f_2), \quad (45)$$

where the penalty parameters $\beta_1$ and $\beta_2$ control the degree of influence of the penalty terms $\Lambda(f_1)$ and $\Lambda(f_2)$, respectively. Although there are many possible choices for the penalty function $\Lambda$, in this approach the following function is used:

$$\overline{\Lambda}(g) = (\Sigma_{j>j_0}^{J-1} g_j)^2 \quad (46)$$

where g is a real J×1 vector. It can be seen that $\Lambda(g)$ is the energy of g after the user chosen time frame $j_0$.

The desired MM algorithm is obtained by setting the partial derivatives of $r(f, f^{(n)}, c^{(n+1)}) + \beta_1 \Lambda(f_1) + \beta_2 \Lambda(f_2)$ with respect to f to zero. For k=1, 2, the partial derivatives of the penalty function $\Lambda$ are $$\frac{\partial \Lambda(f_k)}{\partial f_{j'k'}} = \begin{cases} 2f_{j'k'} & j' > j_0, k' = k \\ 0, & \text{otherwise}, \end{cases} \quad (47)$$

Using this result and equation (27), the following iterative algorithm is derived for estimating the right and left ventricle tissue curves $$f_{jk}^{(n+1)} = f_{jk}^{(n)} \frac{\sum_{i=1}^{I} c_{ik}^{(n+1)} a_{ij}}{\sum_{i=1}^{I} c_{ik}^{(n+1)} \hat{a}_{ij}(c^{(n+1)}, f^{(n)}) + \beta_k f_{jk}^{(n)} I_S(j)}, \quad (48)$$

$$j = 0, 1, 2, \ldots, J-1, k=1, 2$$

where I is the indicator function and $S = \{j_0+1, j_0+2, \ldots, J\}$ (i.e., $I_S(j)=1$ for $j \in S$ and $I_S(j)=0$ for $j \exists S$). The updates for the factor weights and tissue curve (i.e., $f_3$) are given by equations (28) and (29), respectively. The proposed algorithm, refer to herein as the PLS algorithm, monotonically decreases the penalized least-squares (PLS) objective function in equation (45) and is guaranteed to produce nonnegative estimates for the values of the factor curves, f, and factor weights, c. It should be noted that the PLS algorithm provides least-squares estimates when $\beta_1 = \beta_2 = 0$. Also, the update for the factor weights is the same for both the LS and PLS algorithms.

Due to the normegativity of the factor curves for the right and left ventricles, another penalty function optionally can be used to account for the fact that they decrease for t sufficiently large is $$\overline{\Lambda}(g) = (\Sigma_{j>j_0}^{J-1} g_j)^2 \quad (49)$$

Also, with a small modification, the PLS framework can incorporate other known penalty functions.

Exploit Fact that Maximum of Right and Left Ventricle Tissue Curves can be Reliably Estimated When the radiopharmaceutical is administered to a patient, the physiology of the body is such that the activity shows up in the right ventricle first, then the left ventricle, and finally the myocardium. These delays are such that the maximum values of the right and left ventricles are essentially free of activity from the myocardium, despite the motion of the heart and point spread function of the PET system. Thus, an estimate of the maximum value of the right ventricle can be estimated by averaging the maximum values of TACs that lie in the central region of the right ventricle. In a similar way, an estimate of the maximum value of the left ventricle can be obtained. Methods are available that identify the voxels that lie in the right and left ventricles, and myocardium.

Let $\mu_1$ and $\mu_2$ represent the unknown maximum values of the right and left ventricles, respectively, and $j_1$ and $j_2$ denote the locations of the maximum values of the right and left ventricles. To incorporate knowledge of $\mu_i$ and $_j A_2$, we estimate the tissue factors using $$f_{(n+1)} = \arg\min r(f, f^{(n)}, c^{(n)}) \text{ subject to } f \geq 0, |f_{j_1 1} - \hat{\mu}_1| \leq \epsilon,$$
$$|f_{j_2 2} - \hat{\mu}_2| \leq \epsilon \quad (50)$$

where $\epsilon$ is a tolerance parameter chosen by the user, and $\hat{\mu}_1$ and $\hat{\mu}_2$ are estimates of the maximum values $\mu_1$ and $\mu_2$.

The function $r(f, f^{(n)}, c^{(n)})$ is decoupled in the sense that there are no terms of the form $f_{jk}f_{j'k'}$, except when j=j' and k=k'. Thus, the solution to the optimization problem in equation (50) is straightforward and leads to the following update for the right and left ventricle tissue factors (i.e., k=1, 2):

$$f_{jk}^{(n+1)} = f_{jk}^{(n)} \frac{\sum_{i=1}^{I} c_{ik}^{(n+1)} a_{ij}}{\sum_{i=1}^{I} c_{ik}^{(n)} \hat{a}_{ij}(c^{(n+1)}, f^{(n)})}, j \neq j_k, k = 1, 2 \quad (51)$$

-continued $$f_{jk}^{(n+1)} = \left[ f_{jk}^{(n)} \frac{\sum_{i=1}^{I} c_{ik}^{(n+1)} a_{ij}}{\sum_{i=1}^{I} c_{ik}^{(n)} \hat{a}_{ij}(c^{(n+1)}, f^{(n)})} \right]_{\mu_k - \varepsilon}^{\mu_k + \varepsilon}, j \neq j_k, k = 1, 2 \quad (52)$$

where $$[a]_l^u \overset{\Delta}{=} \begin{cases} a, & l \leq a \leq u \\ l, & a < l \\ u, & a > u \end{cases} \quad (53)$$

The updates for the factor weights and tissue curve are given by equations (28) and (29), respectively. Also, the denominator terms in equations (51) and (52) would be $\Sigma_{i=1}^I c_{ik}^{(n+1)} \hat{a}_{i,j}$ $(c^{(n+1)}, f^{(n)}) + \beta_k f_{jk}^{(n)} I_S(j)$ if we included the penalties on the right and left ventricle tissue curves that were discussed in the previous section.

Reduce Unknown Parameters Via a Suitable Model for Left Ventricle Tissue Curve

It has been postulated that the left ventricle tissue curve can be modeled as the convolution of the right ventricle tissue curve with a gamma function. Described below is an exploitation of this idea and development of an extension of the standard least-squares algorithm that has significantly fewer unknowns.

1) Model: Let $r(t)$ and $l(t)$ denote the unknown continuous-time tissue curves for the right and left ventricles, respectively. The left ventricle tissue curve is modeled as the convolution of the right tissue curve with a delayed, gamma function $\bar{h}_c(t)$ $$l(t) = r(t) * \bar{h}_c(t-\tau), \quad (54)$$

where "*" denotes the convolution operator $$\bar{h}_c(t) = a \frac{t^{m-1}}{(m-1)!} \exp(-bt) u(t)$$

$(a > 0, b > 0, \text{ and } m = 1, 2, \ldots), u(t)$ is the unit step function, and $\tau > 0$ is the delay. It should be noted that the delay is due to the fact that the radiopharmaceutical activity first appears in the right ventricle and then the left ventricle. From (54) it follows that $L(s) = R(s) \bar{H}_c(s) \exp(-s\tau)$, where $$\bar{H}_c(s) \overset{\Delta}{=} \frac{a}{(s+b)^m}. \quad (55)$$

As noted previously, we let $f_{j1}$ and $F_{j2}$, $j=0, 1, 2, \ldots, J-1$ denoted the sampled right and left ventricle tissue curves. Where the scan durations for dynamic sequence PET protocols are not uniform, the assumption that the TACs are sampled uniformly is inappropriate. However, uniform samples of the TACs can be obtained from non-uniform samples of the TACs via a suitable interpolation. It is of interest to determine a discrete-time system with the property that its response to the right ventricle tissue curve $f_1$ closely approximates the left ventricle tissue curve $f_2$. The bilinear transformation is a popular way to transform a linear time-invariant continuous-time system into a linear time-invariant discrete-time system. A limitation of the bilinear transform is that a delay in a continuous-time system must be an integer multiple of the sampling interval. Assuming the delay $\tau$ is a multiple of the sampling interval $T_s$, the system function of the desired discrete time system, $H(z)$, can be obtained by applying the bilinear transformation to the continuous-time system $H_c(s) = \bar{H}_c(s) \exp(-s\tau)^3$ $$H(z) = H_c(s) \Big|_{s = \frac{2}{T} \frac{1-z^{-2}}{1+z^{-1}}} \quad (56)$$

$$= a \left[ \frac{1}{(s+b)^m} \Big|_{s=\frac{2}{T}\frac{1-z^{-2}}{1+z^{-1}}} \right] z^{-d} \quad (57)$$

$$= g \left( \frac{1+z^{-1}}{1-pz^{-1}} \right)^m z^{-d}, \quad (58)$$

where $\tau = dT_s$ for some integer $d$, $g = a(2/T_s+b)^{-(m+1)}$, and $p = (2/T_s+b)^{-1}(2/T_s-b)$ (note: $h_c(t) \overset{\Delta}{=} \bar{h}_c(t-\tau T)$).

Let $hj(\theta)$ denote the inverse z-transform of $H(z)$, using a notation that illustrates its dependence on the parameters $\theta = (g, p, m, d)$. Then, the assumed relationship between the sampled right ventricle and left ventricle tissue curves can be written as $$f_{j2} = f_{j1} * h_j(\theta) = \Sigma_{s=0}^{J-1} f_{s1} h_{j-s}(\theta) \quad (59)$$

where, for simplicity, our notation for $f_{j2}$ does not account for its dependence on $\theta$. Moreover, the corresponding least-squares objective function, $L_\theta$, has the same form as L (see equation (4))

$$L_\theta(c, f_1, f_3, \theta) = \sum_{i=1}^{I} \sum_{j=0}^{J-1} \left( a_{ij} - \sum_{k=1}^{K} c_{ik} f_{jk} \right)^2, \quad (60)$$

except it depends on $\theta$ because $f_{j2} = f_{j1} * h_j(\theta)$. To insure that $h_j(\theta)$ is a nonnegative function, the following feasible set for $\theta$ is chosen:

$$D_\theta \overset{\Delta}{=} \{g, p, m, d: g \geq 0, 0 \leq p \leq 1, m = 0, 1, 2, \ldots, d = 0, 1, 2, \ldots\}. \quad (61)$$

Hence, for $\theta \in D_\theta$, $f_{j2}$ is a nonnegative function provided $f_{j1}$ is a nonnegative function.

Convolution Least-Squares Algorithm

Given the similarity of $L_\theta$ and $L$, it follows that the corresponding majorizing functions for $L_\theta$ are $$q_\theta(c, c^{(n)}, f_1, f_3, \theta) \overset{\Delta}{=} \quad (62)$$

$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c^{(n)}, f) \sum_{k=1}^{K} \frac{c_{ik}^2}{c_{ik}^{(n)}} f_{jk} \right\}$$

$$r_\theta(f_1, f_3, f_1^{(n)}, f_3^{(n)}, c, \theta) \overset{\Delta}{=} \quad (63)$$

$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c, f^{(n)}) \sum_{k=1}^{K} \frac{f_{jk}^2}{f_{jk}^{(n)}} c_{ik} \right\}$$

where, again, $fj2 = fj1 * hj(\theta)$. By construction, for all $c$, $c^{(n)} \in D_c$, $f_1, f_3 \geq 0$, and $\theta \in D_\theta$, $$q_\theta(c, c^{(n)}, f_1, f_3, \theta) \geq L_\theta(c, f_1, f_3, \theta) \quad (64)$$

$$q_\theta(c, c, f_1, f_3, \theta) = L_\theta(c, f_1, f_3, \theta) \quad (65)$$

$$r_\theta(f_1, f_3, f_1^{(n)}, f_3^{(n)}, c, \theta) \geq L_\theta(c, f_1, f_3, \theta) \quad (66)$$

$$r_\theta(f_1, f_3, f_1, f_3, c, \theta) = L_\theta(c, f_1, f_3, \theta) \quad (67)$$

Using the MM methodology, the updates for estimating the factor weights and tissue curves, given the current parameters estimates, are given by $$c^{(n+1)} = \arg\min_{c \geq 0} q_\theta(c, c^{(n)}, f_1^{(n)}, f_3^{(n)}, \theta^{(n)}) \quad (68)$$

$$(f_1^{(n+1)}, f_3^{(n+1)}) = \arg\min_{f_1, f_3 \geq 0} r_\theta(f_1, f_3, f_1^{(n)}, f_3^{(n)}, c^{(n+1)}, \theta^{(n)}) \quad (69)$$

$$\theta^{(n+1)} = \arg\min_{\theta \in D_\theta} L_\theta(c^{(n+1)}, f_1^{(n+1)}, f_3^{(n+1)}, \theta) \quad (70)$$

The optimization problem in equation (69) is not straightforward because the objective function in (69) has "cross terms" of the form $f_{j1} f_{j'1}$, $j \neq j'$. These cross terms are due to the $f_{j2}^2$ term in equation (63). Thus, it will be beneficial to construct a majorizing function for $f_{j2}^2$. It is straightforward to show that the steps used to derive the inequality in equation (22) can be repeated to get the following inequality $$f_{j2}^2 \leq v(f_1, f_1^{(n)}, \theta) \triangleq \left[\sum_{s'=0}^{J-1} f_{s'1}^{(n)} h_{j-s'}(\theta)\right] \sum_{s=0}^{J-1} h_{j-s}(\theta) \frac{f_{s1}^2}{f_{s1}}, \quad (71)$$

which has the property that $v(f_1, f_1, \theta) = f_{j2}^2$ for all $f_1 \geq 0$ and $\theta \in D_\theta$. Now, equation (71) is substituted into equation (63) to get a majorizing function that satisfies equations (66) and (67) and can be easily minimized with respect to $f_1$ $$\bar{r}_\theta(f_1, f_3, f_1^{(n)}, f_3^{(n)}, c, \theta) \triangleq \quad (72)$$

$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c, f^{(n)}) \quad (73) \right.$$

$$\left. \left( c_{i1} \frac{f_{j1}^2}{f_{j1}^{(n)}} + c_{i1} \sum_{s=0}^{J-1} h_{j-s}(\theta) \frac{f_{s1}^2}{f_{s1}} + c_{i3} \frac{f_{j3}^2}{f_{j3}^{(n)}} \right) \right\},$$

where $$f_{j2}^{(n)} = f_{j1}^{(n)} * h_j(\theta^{(n)}) = \sum_{s=0}^{J-1} f_{s1}^{(n)} h_{j-s}(\theta^{(n)}) \quad (74)$$

Comparing equations (24) with (62), and (25) with (63), it is evident that the update for the factor weights c (see equation (68)) and the third factor curve $f_3$ (see equation (69)) are given by equations (28) and (29), respectively, except that now $f_{j2}^{(n)}$ is given by equation (74). In order to get the update for the right ventricle $f_1$ (see equation (69)), we take the partial derivative of $\bar{r}_\theta((f_1, f_3, f_1^{(n)}, f_3^{(n)}, c^{(n+1)}, \theta^{(n)}))$ with respect to $f_1$ and set the result to zero. From straightforward calculations, the derivative of $\bar{r}_\theta((f_1, f_3, f_1^{(n)}, f_3^{(n)}, c^{(n+1)}, \theta^{(n)}))$ with respect to $f_{j'1}$ is $$\frac{\partial \bar{r}_\theta(f_1, f_3, f_1^{(n)}, f_3^{(n)}, c^{(n+1)}, \theta^{(n)})}{\partial f_{j'1}} = \quad (75)$$

$$-2\sum_{i=1}^{I} \sum_{j=0}^{J-1} c_{i1} a_{ij'} - 2\sum_{i=1}^{I} \sum_{j=0}^{J-1} c_{i2} a_{ij} h_{j-j'}(\theta^{(n)}) +$$

-continued $$2\frac{f_{j'1}}{f_{j'1}^{(n)}} \sum_{i=1}^{I} c_{i1} \hat{a}_{ij'}(c^{(n+1)}, f^{(n)}) +$$

$$2\frac{f_{j'1}}{f_{j'1}^{(n)}} \sum_{i=1}^{I} \sum_{j=0}^{J-1} c_{i2} \hat{a}_{ij'}(c^{(n+1)}, f^{(n)}) h_{j-j'}(\theta^{(n)}) = -2\sum_{i=1}^{I} c_{i1} a_{ij} -$$

$$2\sum_{i=1}^{I} c_{i2}[a_{ij} * h_{-j'}(\theta^{(n)})] + 2\frac{f_{j'1}}{f_{j'1}^{(n)}} \sum_{i=1}^{I} c_{i1} \hat{a}_{ij'}(c^{(n+1)}, f^{(n)}) +$$

$$2\frac{f_{j'1}}{f_{j'1}^{(n)}} \sum_{i=1}^{I} c_{i2}[\hat{a}_{ij'}(c^{(n+1)}, f^{(n)}) * h_{-j'}(\theta^{(n)})]. \quad (76)$$

Now, equation (76) is set to zero to get the desired update for the right ventricle tissue curve, which is $$f_{j1}^{(n+1)} = f_{j1}^{(n)} \frac{\sum_{i=1}^{I} c_{i1} a_{ij} + \sum_{i=1}^{I} c_{i2}[a_{ij} * h_{-j}(\theta^{(n)})]}{\sum_{i=1}^{I} c_{i1} \hat{a}_{ij}(c^{(n+1)}, f^{(n)}) + \sum_{i=1}^{I} c_{i2}[\hat{a}_{ij}(c^{(n+1)}, f^{(n)}) * h_{-j}(\theta^{(n)})]}, j \quad (77)$$

$$= 0, 1, \ldots, J-1.$$

When knowledge about the maximum value of the right ventricle tissue curve is incorporated, as well as the penalty function A, then the update for the right ventricle tissue curve is $$f_{j1}^{(n+1)} = \left[ f_{j1}^{(n)} \frac{\sum_{i=1}^{I} c_{i1} a_{ij} + \sum_{i=1}^{I} c_{i2}[a_{ij} * h_{-j}(\theta^{(n)})]}{\sum_{i=1}^{I} c_{i1} \hat{a}_{ij}(c^{(n+1)}, f^{(n)}) + \sum_{i=1}^{I} c_{i2}[\hat{a}_{ij}(c^{(n+1)}, f^{(n)}) * h_{-j}(\theta^{(n)})]} \right]_{\mu_k - \epsilon}^{\mu_k + \epsilon}, j \quad (78)$$

$$= 0, 1, \ldots, J-1.$$

With the update for the right ventricle curve in hand (i.e., update in equations (77) or (78)), the algorithm for minimizing the least-squares function $L_\theta$, is proposed, which is referred to herein as the convolution least-squares (CLA) algorithm. First, let $d_{min}$ and $d_{max}$ denote the minimum and maximum delay considered, respectively, and $m_{max}$ denote the maximum value considered for the parameter m. The CLA algorithm follows:

$$\text{get initial estimates: } f_1^{(0)}, f_3^{(0)}, g^{(0)}, \text{ and } p^{(0)} \quad (79)$$

for $\hat{d} = d_{min}, d_{min} + 1, \ldots, d_{max}$, for $\hat{m} = 1, 2, \ldots, m_{max}$, for $n = 0, 1, 2, \ldots$ let $\theta^{(n)} = [g^{(n)} \; p^{(n)} \; \hat{m} \; \hat{d}]$ get $c^{(n+1)}$ using (28) with $f_{j2}^{(n)}$ given by (74)

get $f_1^{(n+1)}$ using (77)

-continued get $f_3^{(n+1)}$ using (29) with $f_{j2}^{(n)}$ given by (74)

$$(g^{(n+1)}, p^{(n+1)}) = \arg\min_{\theta \geq 0, 0 \leq p \leq 1} L_\theta(c^{(n+1)}, f_1^{(n+1)}, f_3^{(n+1)}, g, p, \hat{m}, \hat{d})$$

end store current parameter estimates
and corresponding value for $L_\theta$ end end The desired parameter estimates are the estimates from the CLA algorithm that produce the smallest least-squares error. It should be noted that the objective function $L_\theta$ decreases monotonically with increasing iterations.

The problem in equation (79) can be solved using the following iterative coordinate descent method. It will be convenient to express $h_j(\theta)$ as $h_j(\theta) = g\bar{h}_j(p, m, d)$, where $\bar{h}_j(p, m, d)$ is the inverse Z-transform of $$\bar{H}(z) = \left(\frac{1+z^{-1}}{1-pz^{-1}}\right)^m z^{-d}. \tag{80}$$

With this notation, the objective function in (79) can be written as $$L_\theta(c^{(n+1)}, f_1^{(n+1)}, f_3^{(n+1)}, g, p, \hat{m}, \hat{d}) = \alpha^{(n+1)}g^2 - 2\beta^{(n+1)}g + \gamma^{(n+1)}, \tag{81}$$

where $$\alpha^{(n+1)}(c^{(n+1)}, f_1^{(n+1)}, f_3^{(n+1)}) \triangleq \tag{82}$$

$$\sum_{i=1}^{I}\sum_{j=0}^{J-1}[a_{ij} - (c_{i1}^{(n+1)}f_{j1}^{(n+1)} + c_{i3}^{(n+1)}f_{j3}^{(n+1)})]$$

$$\beta^{(n+1)}(c^{(n+1)}, f_1^{(n+1)}, f_3^{(n+1)}, p, \hat{m}, \hat{d}) \triangleq \tag{83}$$

$$\sum_{i=1}^{I}\sum_{j=0}^{J-1}[a_{ij} - (c_{i1}^{(n+1)}f_{j1}^{(n+1)} + c_{i3}^{(n+1)}f_{j3}^{(n+1)})] \times c_{i2}^{(n+1)}(f_{j1}^{(n+1)} * \hat{h}_j(\hat{p}, \hat{m}, \hat{d}))$$

$$\gamma^{(n+1)}(c^{(n+1)}, f_1^{(n+1)}, f_3^{(n+1)}, p, \hat{m}, \hat{d}) \triangleq \tag{84}$$

$$\sum_{i=1}^{I}\sum_{j=0}^{J-1}[c_{i2}^{(n+1)}(f_{j1}^{(n+1)} * \hat{h}_j(\hat{p}, \hat{m}, \hat{d}))]^2.$$

Thus, the unconstrained minimizer of $L_\theta(c^{(n+1)}, f_1^{(n+1)}, f_3^{(n+1)}, g, \hat{p}, \hat{m}, \hat{d})$ with respect to g is simply $$\hat{g} = \frac{\beta^{(n+1)}(c^{(n+1)}, f_1^{(n+1)}, f_3^{(n+1)}, \hat{p}, \hat{m}, \hat{d})}{\alpha^{(n+1)}(c^{(n+1)}, f_1^{(n+1)}, f_3^{(n+1)}, \hat{p}, \hat{m}, \hat{d})}, \tag{84}$$

where $\hat{p}$ denotes the current estimate for the filter parameter p. With the above result, the steps for solving the optimization problem of equation (79) is given using the coordinate descent method: Let $p^{old} = p_{(n)}$ and $[x]_+ = \max(0, x)$ IC Step 1:

$$g^{new} = \arg\min_{g \geq 0} L_\theta(c^{(n+1)}, f_1^{(n+1)}, f_3^{(n+1)}, g, p^{old}, \hat{m}, \hat{d}) \tag{84}$$

$$= \left[\frac{\beta^{(n+1)}(c^{(n+1)}, f_1^{(n+1)}, f_3^{(n+1)}, p^{old}, \hat{m}, \hat{d})}{\alpha^{(n+1)}(c^{(n+1)}, f_1^{(n+1)}, f_3^{(n+1)}, p^{old}, \hat{m}, \hat{d})}\right]_+, \tag{87}$$

IC Step 2: Using a 1D line search, such as the golden section method [17], get $p^{new}$:

$$p^{new} = \arg\min_{0 \leq p \leq 1} L_\theta(c^{(n+1)}, f_1^{(n+1)}, f_3^{(n+1)}, g^{new}, p, \hat{m}, \hat{d}) \tag{88}$$

IC Step 3: Set $g^{old} = p^{new}$ and repeat the above two steps, for a set number of iterations or until some desired stopping criterion is met.

IC Step 4: Set $g^{(n+1)} = g^{new}$ and $p^{(n+1)} = p^{new}$.

So configured, the CLA algorithm is monotonic and guaranteed to produce nonnegative estimates.

Initialization

User-dependent and user-independent methods are available for determining initial estimates for the right and left ventricle tissues curves, and myocardial tissue curve. The initial factor weights are typically chosen to be uniform in the sense that $c_{ik} = 1/3$ for all i, k. Regarding the range of values for the delay, suitable values for the minimum and maximum delay between the right and left ventricle tissue curves are available from the literature in human physiology.

It is expected that a suitable maximum value for the filter order, $m_{max}$, can be determined through experiments. Consequently, the following addresses computing initial estimates for the filter parameters g and p.

Because $F_2(z) = H(z)F_1(z)$ from equation (59), it follows that $F_2^{(0)}(z) \approx H(z)F_1^{(0)}(z)$, where $f_{1j}^{(0)}$ and $f_{2j}^{(0)}$ denote the initial right and left ventricle tissue curves, and $H(z)$ is given by equation (58). Therefore, $$F_2^{(0)}(z) \approx H(z) \approx F_1^{(0)}(z) \tag{89}$$

$$F_2^{(0)}(z) \approx g\left(\frac{1+z^{-1}}{1-pz^{-1}}\right)^m z^{-d} F_1^{(0)}(z) \tag{90}$$

$$F_2^{(0)}(z) \approx g\frac{1}{(1-pz^{-1})^m} z^{-d} \bar{F}_1^{(0)}(z) \tag{91}$$

where $$\bar{F}_1^{(0)}(z) = F_1^{(0)}(z)(1-z^{-1})^m z^{-d}. \tag{92}$$

Thus, the initial left ventricle tissue curve is assumed to be approximately equal to the response of a certain mth-order, all-pole filter to the initial right ventricle tissue curve. This observation and equation (91) forms the basis of the following method for obtaining initial estimates for g and p:

for $\hat{d} = d_{min}, d_{min}+1, \ldots, d_{max}$, for $m = 1, 2, \ldots, m_{max}$, Initial g, p—Step 1: Using an input-output system identification method, such as the Steiglitz-McBride algorithm, find the parameters $b_0, a_1, a_2, \ldots, a_m$ that provide the best least-squares fit for the following model:

$$F_2^{(0)}(z) = b_0 \frac{1}{(1 + a_1 z^{-1} + a_2 z^{-2} + \ldots + a_m z^{-m})} \overline{F}_1^{(0)}(z) \quad (93)$$

Initial g, p—Step 2: Let $\hat{b}_0, \hat{a}_1, \hat{a}_2, \ldots, \hat{a}_m$ be the resulting estimates for $b_0, a_1, a_2, \ldots, a_m$, respectively, from the first step. Comparing equations (91) and (93), an estimate for g is $\hat{g} = \hat{b}_0$. Moreover, an estimate for p can be obtained by determining the best least-squares fit between $(1-pz^{-1})^m$ and $(1+a_1z^{-1}+a_2z^{-2}+\ldots+a_mz^{-m})$. For Example, when m=2, an estimate for p is:

$$\hat{p} = \arg\min_{0 \le p \le 1} (-2p - \hat{a}_1)^2 + (p^2 - \hat{a}_2)^2, \quad (94)$$

Initial g, p—Step 3: Store the current parameter estimates $\{\hat{g}, \hat{p}, \hat{m}, \hat{d}\}$ and the corresponding least-squares error $$L_{int}(\hat{g}, \hat{p}, \hat{m}, \hat{d}) \triangleq \sum_{j=0}^{J-1} \left(f_{j2}^{(0)} - \overline{f}_{j1}^{(0)}(\hat{m}, \hat{d}) * \overline{h}_j(\hat{g}, \hat{p}, \hat{m})\right)^2, \quad (95)$$

where $\overline{f}_{j1}^{(0)}(\hat{m}, \hat{d})$ and $\overline{h}_j(g, p, m)$ are, respectively, the inverse Z-transforms of $\overline{F}_1^{(0)}(z)$ (see (92)) and $$\overline{H}(z) \triangleq g \frac{1}{(1 - pz^{-1})^m}. \quad (96)$$

end end

The set of parameters that produce the smallest least-squares error are the desired initial estimates for the parameters g, p, m, and d, which we denote respectively as $g^{(0)}$, $p^{(0)}$, $m^{(0)}$, and $d^{(0)}$.

The initial estimates for the parameters m and d are not explicitly used in the CLA algorithm. However, they could be used to reduce the range of values considered for the parameters m and d. For example, the "for loop" for the delay in the CLA algorithm could be instead: for $\hat{d} = d^{(0)} - \Delta : d^{(0)} + \Delta$, where $\Delta > 0$, would be an integer chosen by the user.

III. Implementation of the Algorithms

Figure 3:
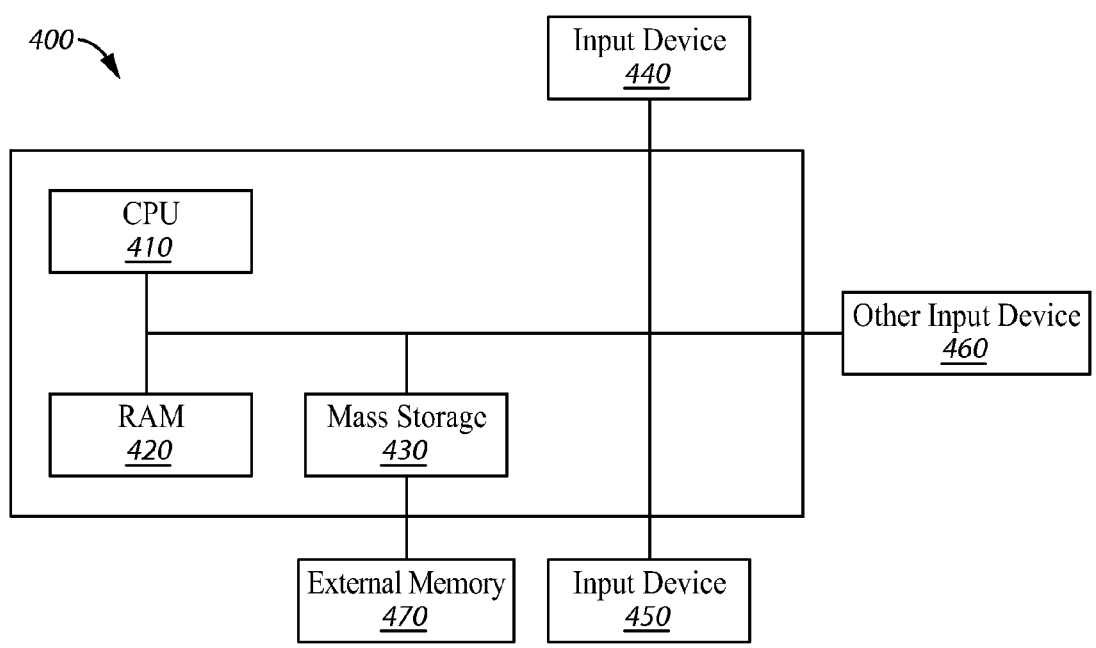
FIG. 3 illustrates an embodiment of a illustrative system that can incorporate the present embodiments.

The methods and techniques described in the various approaches above may be utilized, implemented, and/or run on many different types of systems, including for example computers, game consoles, entertainment systems, etc. Referring to FIG. 3, a system 400 is illustrated that may be used for any such implementations. One or more components of the system 400 may be used for implementing any system or device mentioned above, such as for example even a handheld device. However, the use of the system 400 or any portion thereof is not necessarily required.

By way of example, the system 400 may include, but is not required to include, a central processing unit (CPU) 410, a random access memory (RAM) 420, and a mass storage unit 430, such as a disk drive. The system 400 may be coupled to, or integrated with, any of the other components described herein, such as an input device 450, 460 and other input device 470. The system 400 comprises an example of a processor based system. The CPU 410 may be used to execute or assist in executing the steps of the methods and techniques described herein. In one approach, the system 400 may further comprise a graphics processing unit to execute or assist in executing the steps of the methods and techniques described herein. In some embodiments, the input device 450 may comprise a first touch sensitive panel and the input device 460 may comprise a second touch sensitive panel. Furthermore, in another aspect, the system 400 comprises another input device 460 that may comprise other user input means such as buttons, keyboard, mouse, joystick, and the like. In another aspect, other input device 460 may further comprise output means, such as displays, sound emitters, light emitters, and the like configured to. In one embodiment one or more of the input device 450, input device 460 and other input device 470 comprise display functionality. In one embodiment various program content, images, shadows, lighting, and the like may be rendered on one or more of the input device 450, 460 and other input device 470.

The mass storage unit 430 may include or comprise any type of computer readable storage or recording medium or media. The computer readable storage or recording medium or media may be fixed in the mass storage unit 430, or the mass storage unit 430 may optionally include external memory 470, such as a digital video disk (DVD), Blu-ray disc, compact disk (CD), USB storage device, floppy disk, or other media. By way of example, the mass storage unit 430 may comprise a disk drive, a hard disk drive, flash memory device, USB storage device, Blu-ray disc drive, DVD drive, CD drive, floppy disk drive, and the like. The mass storage unit 430 or external memory 470 may be used for storing program code or macros that implement the methods and techniques described herein.

Thus, external memory 470 may optionally be used with the mass storage unit 430, which may be used for storing program code that implements the methods and techniques described herein. However, any of the storage devices, such as the RAM 420 or mass storage unit 430, may be used for storing such program code. For example, any of such storage devices may serve as a tangible computer readable storage medium for storing or embodying a computer program for causing a console, system, computer, or other processor based system to execute or perform the steps of any of the methods, code, and/or techniques described herein. Furthermore, any of the storage devices, such as the RAM 420 or mass storage unit 430, may be used for storing any needed database(s), gestures, lists, macros, etc.

In some embodiments, one or more of the embodiments, methods, approaches, and/or techniques described above may be implemented in a computer program executable by a processor based system. By way of example, such processor based system may comprise the processor based system 400, or a computer, console, graphics workstation, and the like. Such computer program may be used for executing various steps and/or features of the above-described methods and/or techniques. That is, the computer program may be adapted to cause or configure a processor based system to execute and achieve the functions described above. For example, such computer program may be used for implementing any embodiment of the above-described steps or techniques for performing a task at the handheld device. As another example, such computer program may be used for implementing any type of tool or similar utility that uses any one or more of the above described embodiments, methods, approaches, and/or techniques. In some embodiments, the computer program may comprise a computer simulation, or system software such as an operating system, BIOS, macro, or other utility. In some embodiments, program code macros, modules, loops, subroutines, etc., within the computer program may be used for executing various steps and/or features of the above-described methods and/or techniques. In some embodiments, the computer program may be stored or embodied on a computer readable storage or recording medium or media, such as any of the computer readable storage or recording medium or media described herein.

Therefore, in some embodiments a computer program product comprising a non-transitory medium for embodying a computer program for input to a computer and a computer program embodied in the medium for causing the computer to perform or execute steps comprising any one or more of the steps involved in any one or more of the embodiments, methods, approaches, and/or techniques described herein.

While the methods and systems have been described in conjunction with specific embodiments, it is evident that many alternatives, modifications, and variations will be apparent to those skilled in the art in light of the foregoing description.

What is claimed is:

1. A method for estimating myocardial blood flow, the method comprising:
   a processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:
      incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;
   the processing device outputting a processed data set based on the application of the pharmacological kinetic model to the data set for providing a representation of blood flow in the myocardium; and
   the processing device estimating parameters of the standard factor analysis of dynamic structures model by applying a penalty term to account for time activity curves for the right ventricle imaging activity from the fluid based tracers and the left ventricle imaging activity from the fluid based tracers decaying to zero over time.

2. The method of claim 1 further comprising the processing device estimating parameters of the standard factor analysis of dynamic structures model by estimating maximum values of fluid based tracer activity in one or both of the right ventricle or the left ventricle and modifying a corresponding signal vector value for the one of the right ventricle or the left ventricle using the estimated maximum values of fluid based tracer activity.

3. The method of claim 1 further comprising the processing device estimating parameters of the standard factor analysis of dynamic structures model by:
   estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and
   determining a set of parameters that produce a smallest least-squares error for the pharmacological kinetic model.

4. The method of claim 3 wherein the estimating further comprises for a given initial estimate right ventricle tissue activity curve and a given initial estimated left ventricle tissue activity curve, determining initial estimates for parameters of the pharmacological kinetic model.

5. A non-transitory computer readable medium storing instructions that cause a processing device, in response to executing the instructions, to perform operations comprising:
   the processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:
      incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;
   the processing device outputting a processed data set based on the application of the pharmacological kinetic model to the data set for providing a representation of blood flow in the myocardium; and
   the processing device estimating parameters of the standard factor analysis of dynamic structures model by applying a penalty term to account for time activity curves for the right ventricle imaging activity from the fluid based tracers and the left ventricle imaging activity from the fluid based tracers decaying to zero over time.

6. The non-transitory computer readable medium of claim 5 further comprising instructions to cause the processing device to perform operations comprising estimating parameters of the standard factor analysis of dynamic structures model by estimating maximum values of fluid based tracer activity in one or both of the right ventricle or the left ventricle and modifying a corresponding signal vector value for the one of the right ventricle or the left ventricle using the estimated maximum values of fluid based tracer activity.

7. The non-transitory computer readable medium of claim 5 further comprising instructions to cause the processing device to perform operations comprising estimating parameters of the standard factor analysis of dynamic structures model by:
   estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and
   determining a set of parameters that produce a smallest least-squares error for the pharmacological kinetic model.

8. The non-transitory computer readable medium of claim 7 further comprising instructions to cause the processing device to perform operations comprising for a given initial estimate right ventricle tissue activity curve and a given initial estimated left ventricle tissue activity curve, determining initial estimates for parameters of the pharmacological kinetic model.

9. An apparatus comprising:
   a processing device configured to apply a pharmacological kinetic model to a data set stored in a storage device, the data set derived from an imaging technique based on monitoring fluid based tracers in a left ventricle, a right ventricle, and myocardium, wherein the pharmacological kinetic model includes:
      incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device configured to output a processed data set based on the application of the pharmacological kinetic model to the data set for providing a representation of blood flow in the myocardium; and the processing device configured to estimate parameters of the standard factor analysis of dynamic structures model by applying a penalty term to account for time activity curves for the right ventricle imaging activity from the fluid based tracers and the left ventricle imaging activity from the fluid based tracers decaying to zero over time.

10. The apparatus of claim 9 wherein the processing device is configured to estimate parameters of the standard factor analysis of dynamic structures model by estimating maximum values of fluid based tracer activity in one or both of the right ventricle or the left ventricle and modifying a corresponding signal vector value for the one of the right ventricle or the left ventricle using the estimated maximum values of fluid based tracer activity.

11. The apparatus of claim 9 wherein the processing device is configured to estimate parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

12. The apparatus of claim 11 wherein the estimating further comprises for a given initial estimate right ventricle tissue activity curve and a given initial estimated left ventricle tissue activity curve, determining initial estimates for parameters of the pharmacological kinetic model.

13. A method for estimating myocardial blood flow, the method comprising:

a processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:

incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device outputting a processed data set based on the application of the pharmacological kinetic model to the data set for providing a representation of blood flow in the myocardium; and the processing device estimating parameters of the standard factor analysis of dynamic structures model by estimating maximum values of fluid based tracer activity in one or both of the right ventricle or the left ventricle and modifying a corresponding signal vector value for the one of the right ventricle or the left ventricle using the estimated maximum values of fluid based tracer activity.

14. The method of claim 13 further comprising the processing device estimating parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

15. The method of claim 14 wherein the estimating further comprises for a given initial estimate right ventricle tissue activity curve and a given initial estimated left ventricle tissue activity curve, determining initial estimates for parameters of the pharmacological kinetic model.

16. A method for estimating myocardial blood flow, the method comprising:

a processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:

incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device outputting a processed data set based on the application of the pharmacological kinetic model to the data set for providing a representation of blood flow in the myocardium; and the processing device estimating parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

17. The method of claim 16 wherein the estimating further comprises for a given initial estimate right ventricle tissue activity curve and a given initial estimated left ventricle tissue activity curve, determining initial estimates for parameters of the pharmacological kinetic model.

18. A non-transitory computer readable medium storing instructions that cause a processing device, in response to executing the instructions, to perform operations comprising:

the processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:

incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device outputting a processed data set based on the application of the pharmacological kinetic model to the data set for providing a representation of blood flow in the myocardium; and the processing device estimating parameters of the standard factor analysis of dynamic structures model by estimating maximum values of fluid based tracer activity in one or both of the right ventricle or the left ventricle and modifying a corresponding signal vector value for the one of the right ventricle or the left ventricle using the estimated maximum values of fluid based tracer activity.

19. The non-transitory computer readable medium of claim 18 further comprising instructions to cause the processing device to perform operations comprising estimating parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

20. The non-transitory computer readable medium of claim 19 further comprising instructions to cause the processing device to perform operations comprising for a given initial estimate right ventricle tissue activity curve and a given initial estimated left ventricle tissue activity curve, determining initial estimates for parameters of the pharmacological kinetic model.

21. A non-transitory computer readable medium storing instructions that cause a processing device, in response to executing the instructions, to perform operations comprising:

the processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:

incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device outputting a processed data set based on the application of the pharmacological kinetic model to the data set for providing a representation of blood flow in the myocardium; and the processing device estimating parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

22. The non-transitory computer readable medium of claim 21 further comprising instructions to cause the processing device to perform operations comprising for a given initial estimate right ventricle tissue activity curve and a given initial estimated left ventricle tissue activity curve, determining initial estimates for parameters of the pharmacological kinetic model.

23. An apparatus comprising:

a processing device configured to apply a pharmacological kinetic model to a data set stored in a storage device, the data set derived from an imaging technique based on monitoring fluid based tracers in a left ventricle, a right ventricle, and myocardium, wherein the pharmacological kinetic model includes:

incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device configured to output a processed data set based on the application of the pharmacological kinetic model to the data set for providing a representation of blood flow in the myocardium; and the processing device configured to estimate parameters of the standard factor analysis of dynamic structures model by estimating maximum values of fluid based tracer activity in one or both of the right ventricle or the left ventricle and modifying a corresponding signal vector value for the one of the right ventricle or the left ventricle using the estimated maximum values of fluid based tracer activity.

24. The apparatus of claim 23 wherein the processing device is further configured to estimate parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

25. The apparatus of claim 24 wherein the estimating further comprises for a given initial estimate right ventricle tissue activity curve and a given initial estimated left ventricle tissue activity curve, determining initial estimates for parameters of the pharmacological kinetic model.

26. An apparatus comprising:

a processing device configured to apply a pharmacological kinetic model to a data set stored in a storage device, the data set derived from an imaging technique based on monitoring fluid based tracers in a left ventricle, a right ventricle, and myocardium, wherein the pharmacological kinetic model includes:

incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle;

the processing device configured to output a processed data set based on the application of the pharmacological kinetic model to the data set for providing a representation of blood flow in the myocardium; and the processing device configured to estimate parameters of the standard factor analysis of dynamic structures model by:

estimating a left ventricle tissue activity curve, a right ventricle tissue activity curve, and a tissue activity curve, wherein the left ventricle tissue activity curve is assumed to be approximately equal to a response of an mth-order, all-pole filter applied to the right ventricle tissue activity curve, and determining a set of parameters that produce a smallest least-squares error for the pharmacological kinetic model.

27. The apparatus of claim 26 wherein the estimating further comprises for a given initial estimate right ventricle tissue activity curve and a given initial estimated left ventricle tissue activity curve, determining initial estimates for parameters of the pharmacological kinetic model.

* * * * *